United States Patent [19]
Becker et al.

[11] Patent Number: 5,986,278
[45] Date of Patent: Nov. 16, 1999

[54] FILMLESS PHOTON IMAGING APPARATUS

[75] Inventors: Charles D. Becker, Helotes; Harry Dell Foster, San Antonio; Alfonzo Zermeno, Houston, all of Tex.; Gale H. Thorne, Bountiful; James V. Yardley, Centerville, both of Utah

[73] Assignee: Quantum Imaging Corporation, Bountiful, Utah

[21] Appl. No.: 09/179,078

[22] Filed: Oct. 26, 1998

Related U.S. Application Data

[62] Division of application No. 08/900,541, Jul. 25, 1997.

[51] Int. Cl.[6] .............................. G01T 1/29; G03G 5/04
[52] U.S. Cl. ...................................... 250/580; 250/370.09
[58] Field of Search .................. 250/370.09, 370.06, 250/580

[56] References Cited

U.S. PATENT DOCUMENTS

| | | | |
|---|---|---|---|
| 5,166,524 | 11/1992 | Lee et al. ................................ | 250/580 |
| 5,268,569 | 12/1993 | Nelson et al. ....................... | 250/370.09 |
| 5,508,507 | 4/1996 | Nelson et al. ....................... | 250/370.09 |

*Primary Examiner*—Constantine Hannaher
*Attorney, Agent, or Firm*—Gale H. Thorne; Paul S. Evans

[57] ABSTRACT

Filmless photon imaging sensor plates and apparatus which are particularly effective in medical radiology and industrial applications including, but not limited to high resolution mammography. In combination, the sensor plates and apparatus provide rapid production of high resolution images which exhibit higher sensitivity and wider dynamic range than contemporary X-ray systems. Novel sensor plate structures provide images having attributes of increased sensitivity; dual plate design providing increased pixel read-out speed and differential dual energy image production; and electrically isolated segments by which a plurality of pixels are read concurrently to reduce overall image processing time. Generally, the plates employ a homogeneous photoconductive material such as amorphous selenium and are read by exposing each pixel sized area to a small diameter scanning light beam. Using light beam scanning, resulting plate design promises low cost manufacture of both sensor plates and associated apparatus. Novel application of electric fields during plate preparation, exposure and read-out provides improved sensor plate performance. A plurality of precisely-positioned light beams are scanned across the sensor through the use of a novel optical system employing an elongated light source disposed within a rotating drum, the drum being generally opaque with a helical transparent pattern which in combination with a series of lenses and a slit provides the plurality of precisely-positioned scanning light beams. By changing slit and beam widths, variable resolution operation is achieved.

35 Claims, 18 Drawing Sheets

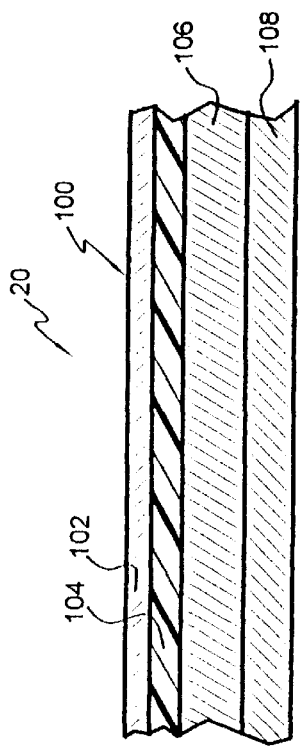
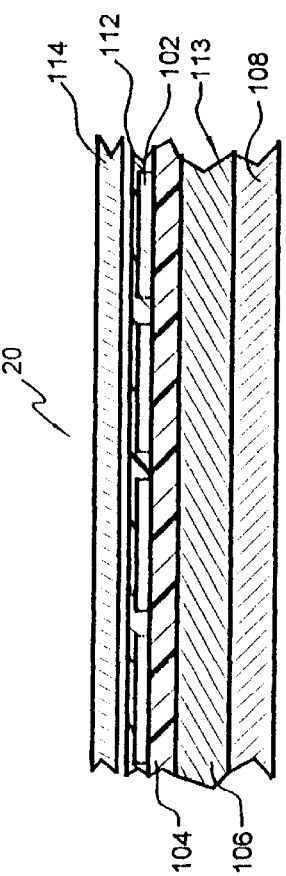
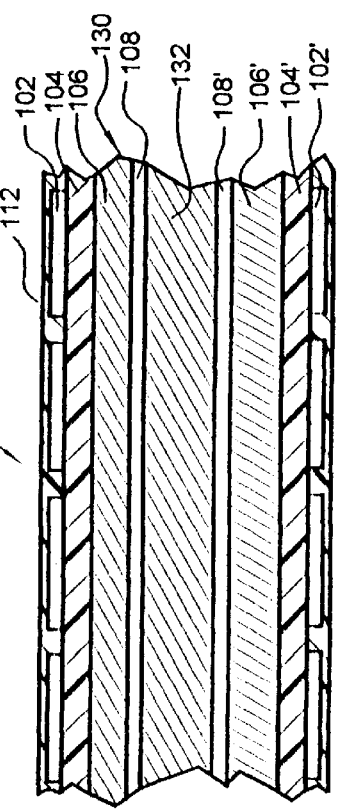
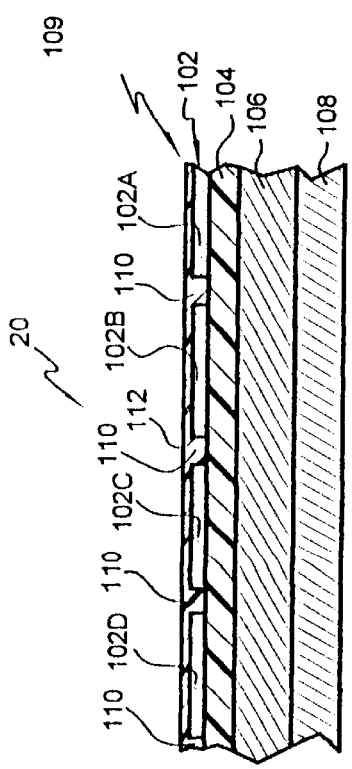
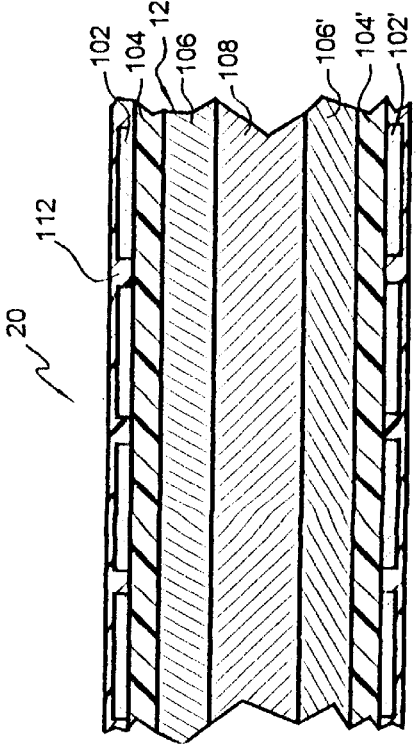
PRIOR ART
Figure 1
Figure 2
Figure 3
Figure 4
Figure 5

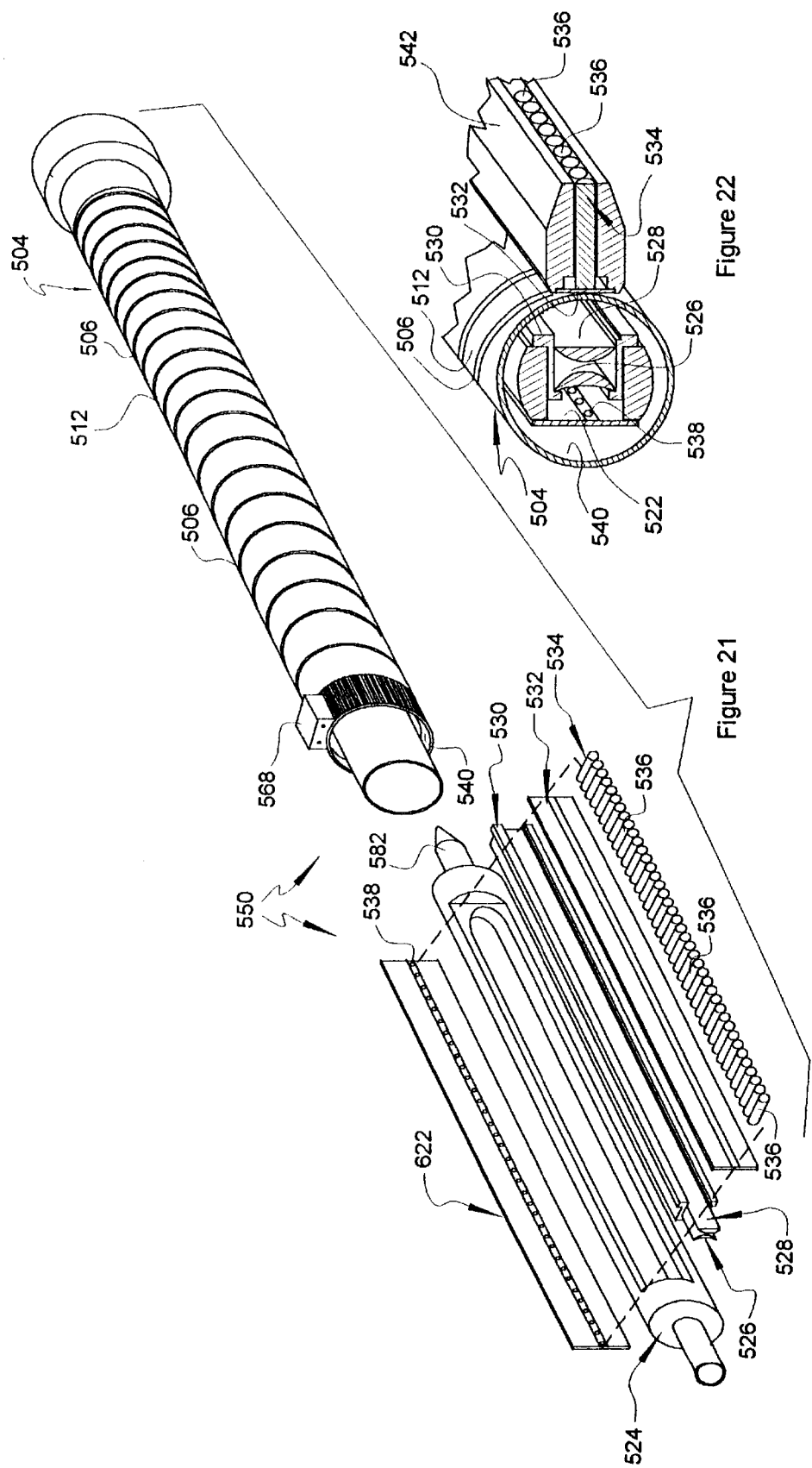

FILMLESS PHOTON IMAGING APPARATUS

This application is a divisional of application Ser. No. 08/900,541, filed Jul. 25, 1997.

FIELD OF INVENTION

This invention relates broadly to filmless x-ray and other photon imaging equipment and methods. For example, in particular, it relates to imaging apparatus having sufficiently high resolution and sensitivity to be safely and efficaciously applied to the area of mammography (x-ray breast imaging), yet having dynamic range characteristics which permit similar safe and effective application to other imaging areas having lower resolution and higher sensitivity requirements. Further, this invention relates to imaging apparatus which rapidly digitizes an image for digital viewing, storing and transmitting.

BACKGROUND

X-ray imaging remains an important contemporary discipline in medical technology. Use of X-ray processes are in common practice in systems which range from real time images, usually of low resolution gastrointestinal sections, taken by image intensifier-vidicon chains, to single shot images, examples of which are chest and mammography studies, normally captured and processed on film.

Although film based systems form the backbone of diagnostic radiology today, presently there is significant motivation to find and employ improved methods. That motivation comprises elimination of expensive and space-consuming photography development laboratories, of large film storage facilities, of levels of x-ray dosage required by film, of cost of silver halide film, of limited resolution in preferably low dose applications such as mammography, of finite and somewhat fixed sensitivity of film processes and of time and associated manpower required to process film itself and deleterious effect of film processing upon the environment.

Even so, at this time, the majority of chest and mammographic x-ray images are produced by film-based systems. A number of systems which produce images without film are currently being sold by FUJI Corporation of Japan, by Kodak and General Electric Corporations of the United States and by Siemans and Phillips Corporations of Germany. Generally, the majority of the above listed companies sell systems based upon FUJI technology which employs photo-stimulable luminescent methodologies. Somewhat differently, the Phillips system employs a selenium surface located on a rotating drum. Generally, these systems are used for chest x-ray imaging and other large body-area studies and have inherent resolution limitations. A first attempt to replace filmless mammographic x-ray processes, by Xerox Corporation, was abandoned due to high dosage requirements. Succeeding refinements reduced x-ray dosage but did not compete well against a rising tide of screen film mammography. This attempt was based upon an electrostatic latent image impressed upon a selenium plate and developed in a manner similar to early production of Xerox photocopying.

While each of the currently marketed filmless systems promises to fulfill an existing market niche, for replacing film based systems, there remains existing radiology requirements for imaging systems which have not been heretofore fulfilled. These requirements include an increase in resolution and a reduction in x-ray dosage for all applications, but foremost for mammography, rapid visual image production, low cost (especially for upgrading present film based systems) and wide dynamic range to void need for image retakes caused by over or under exposure are paramount for providing a commercially viable system. This instant invention provides innovative solutions to the above recited needs while providing a ready answer to other newly recited, but currently unreachable, objectives comprising filmiess image subtraction to draw low contrast images out from high density image shadows and placing x-ray capability in heretofore unreachable environments, such as in emergency vehicles and the weightless environment of space.

DESCRIPTION OF RELATED ART

A review of general background, of art related to this invention prior to July, 1981, is found in U.S. Pat. No. 4,521,808 (referred to hereafter as '808), issued Jun. 4, 1985 to Ong, et al. In '808 and a number of related patents including U.S. Pat. No. 4,446,365 ('365) issued May 1, 1984 to Ong, et al., U.S. Pat. No. 4,763,002 ('002) issued Aug. 9, 1988 to Zermeno, et al. and U.S. Pat. No. 4,539,591 ('591) issued Sep. 3, 1985 to Zermeno, et al., methods and apparatus for recording an electrostatic latent image by placing the latent image on a photoconductive layer of a multilayered detector apparatus are disclosed. Disclosure includes placing a uniform surface charge on the photoconductive layer, biasing of the photoconductive layer with an electric field which opposes the surface charge and discharging a portion of said surface charge by exposing the detector to a modulated radiation flux capable of generating electron hole pairs in the photoconductor to store an image in the detector. The image is read from the detector by scanning and thereby partially further discharging the surface charge with a small diameter photon beam to create a quantity of electron hole pairs which are carriers of charges representing the image. The electron hole pairs resultantly generate an electric current which is detected and used to form a digital embodiment of the image. In particular, '591 discloses pulse modulating a light source between two nanoseconds and ten microseconds to increase detector signal strength, methods for removing "artifacts" due to prior images stored in the detector so the detector can be used repeatedly, repeated scanning of an image to produce successive images, reduction of image development time by pulsing the light source, integrating current generated by each light pulse to determine a digital pixel representation of the spot illuminated by the light pulse and circuits and methods for controlling an x-ray exposure and the effect of internal capacitance of the detector upon detector sensitivity and scan speed. In addition, segmentation of a plate into small sections to reduce detector capacitance and effects of reverse biasing of the detector to increase output signal strength are also disclosed. Although other photoconducting materials may be used, selenium is taught to be preferred.

Generally, multilayered detectors comprise layers of photoconductive material and dielectric material sandwiched between conductive layers. U.S. Pat. No. 4,857,723 ('723), issued Aug. 15, 1989 to Modisette discloses segmentation of the conductive layers for the purposes reducing electrically detectable noise and providing for parallel readout of detector pixels. Specialized apparatus and methods for reading out an image from a layered detector in a parallel mode is generally disclosed in U.S. Pat. No. 5,268,569 ('569) issued Dec. 7, 1993, to Nelson et al., U.S. Pat. No. 5,340,975 ('975) issued Aug. 23, 1994 to Vogelgessang and U.S. Pat. No. 5,354,982 ('982) to Nelson, et al. As an example, '982 discloses a detector comprising a conductive layer adjacent a photoconductive layer which comprises a plurality of elongated parallel conductive stripes. The stripes are selectively scanned in a parallel mode to permit time-ordered detection of charge carriers produced within the photoconductive material. Charge carriers which are generated in an area between the stripes are read by the stripes adjacent the area. To accomplish reading of the entire detector area, electrical signals generated at each pixel area are integrated to achieve precise pixel measurement from a variety of signal waveforms.

A decision tree for determining commercial viability of a filmless radiology system comprises five major inter-related factors. These five major factors are resolution, sensitivity, dynamic range, cost and image processing time. The importance of each of these factors is well demonstrated when reviewing needs associated with mammographic radiology. It is well known in the art that early detection of breast cancer requires regular and frequent screening. Early detection involves willingness of each patient to periodically submit to a screening test, ability to detect very small anomalies (for example, detection limits in the range of 20 line pairs/millimeter (lp/mm)), exposing the patient to as low an x-ray dose as possible (as a target, to not greater than 1.0 Roentgen exposure dose per view), being able to deliver each breast image screening for a cost commensurate with a patient's ability to pay on a continual basis and completing an examination within a reasonably short period of time. Currently, these requirements inter-relate to support a broad set of contemporarily marketed apparati and methods, rather than a single device or process, to effectively satisfy the radiology market needs.

Following is a summary of the factors considered to critically affect perceived product performance and acceptance 1. Resolution For a mammography application, a resolution of 10 lp/mm is considered adequate, but at least 20 lp/mm is preferred. For a system to be usefully employed across a spectrum which comprises both chest x-ray and mammography, a resolution range of 2.5 to 20 or greater lp/mm might be desired.

2. Sensitivity Generally, a prescribed radiation dosage is dependent upon detector sensitivity, but one who is skilled in radiology understands that dose is also dependent upon achieving a desired detector resolution. As an example, a dose which is considered standard for a mammography examination with an expected resolution of 15 lp/mm is approximately 1.0 Roentgen (exposure dose to the patient). It is highly desirable to achieve the same or higher resolution (20 lp/mm or higher) with a lower dose.

3. Dynamic Range A corollary to sensitivity is dynamic range. Applied to more challenging aspects of physiologic imaging, such as requirements which must be met for mammography, dynamic range may be best understood by reviewing detail and quality of images achieved through the use of Xeroradiography (based upon an amorphous selenium sensor) and compared against present-day film-screen images. Xeroradiographic images readily provided a clear vision of not only breast tissue but also of breast structure and matter in the vicinity of the axillary tail and lymph nodes deeply imbedded near the chest wall. As is well known in medicine these near-chest wall regions are predominant areas where tumors originate and are often difficult to see. Even today, film-screen images do not provide such breadth of detail in a single image. Broader dynamic range of selenium provided opportunity for achieving an image with such greater detail in a picture taken by a single x-ray dose rather with pictures taken by multiple doses by contemporary systems having a smaller dynamic range. In addition, broad dynamic range can provide opportunity for acquiring a more complete and diagnostically perceptible image even when a given x-ray dose might lead to unacceptably poor images which are either over or under exposed in systems with less dynamic range such as film or film screen systems. As one who is skilled in digital image processing understands also, providing an image having visually interpretable presentation implies acquiring and storing data which has more detail (more binary data) in each pixel. Thus, a dynamic range of twelve to fourteen binary bits of binary data (greater than three decades of exposure from black to white) per pixel is generally preferred.

4. Imaging Processing Time In digital systems, imaging processing time is generally, directly related to the number of pixels in a given image. In the case of mammography (assuming 20 lp/mm, and 24 centimeter by 30 centimeter detector plate size) the number of pixels may exceed 115,000,000 in one image. As an example, if a reasonable processing time is determined to be 90 seconds, the average processing time per pixel should not exceed $8 \times 10^{-7}$ seconds.

5. Cost is a product of many variables, some of which are:
   a. Amortization of cost of changing over to filmless imaging;
   b. Cost of detector plates (which should be reusable);
   C. Image processing and other technician related time;
   d. Image storage and retrieval; and
   e. Compatibility with diagnostic processing.

Of course, cost may be reduced by using a system which eliminates need for a film developing-and processing laboratory, for storage and retrieval of film and for film image digitization before employing teleradiography. Even so, the character of 1 5 contemporary medicine dictates that great care must be taken to assure a user that change will be cost effective. Currently, average billed cost of a mammogram is considered to be well over $50.00 per screening procedure (see November 1995 issue of Diagnostic Imaging). At the current cost level, it is thought that many women, who are candidates for breast cancer, are not taking advantage of mammographic screening and are therefore increasingly at risk.

6. Other Of course, there are other product features which do not fall into the above categories, yet which affect product viability. Some of which yield to novel solution within the scope of this invention comprise:
   a. Dual energy imaging for separating low absorption image data from the shadow of high absorption material.
   b. Use of intensifying screens (similar to use of phosphor intensifying screens in film screen systems) to absorb x-rays and permit use of photoconductors which are significantly faster hole conductors than selenium or to absorb x-rays to permit use of a thinner photoconductor.

Following is a table which provides definitions, within the scope of this disclosure, of comparative values for each of the critical factors.

| Factor | Low | Medium | High |
| --- | --- | --- | --- |
| Resolution | < four line pairs/millimeter | four to ten line pairs/millimeter | > ten line pairs/millimeter |
| Per Pixel processing rate [80 × 10⁶ pixel Imaging time] | <40,000 pixels/second [>2000 seconds] | 40,000 to 10⁶ pixels/second [80–2000 seconds] | >10⁶ pixels/second [<80 seconds] |
| Cost (Plate or Sensor) | <$1,000 each | $1,000 to $10,000 | >$10,000 |
| Sensitivity (mean glandular dose measured using a mammography phantom) | >.17* 10⁻² Gy | .15 to .17* 10⁻² Gy | <.15* 10⁻² Gy |
| Dynamic Range (lowest sensitivity to saturation) | < four wedge steps (<9 binary bits) - 1 decade of relative exposure | four to six wedge steps (9–10 binary bits) - Approx. 2 decades of relative exposure | >six wedge steps (>10 binary bits) - >3 decades of relative exposure* |

*e.g. range between black and white can range from 1 mR to 1000 mR or .3 mR to 300 mR, etc.
Where:
\> means greater than
< means less than
Gy = 10² rad = 10² cGy
making the low, medium, high Gy ranges in the above table, respectively: .170 cGy, .15 to .17 cGy, .15 cGy.

BRIEF SUMMARY AND OBJECTS OF THE INVENTION

In brief summary, these novel inventions and inventive processes, when used in innovative combination, alleviate all of the known problems related to providing a commercially viable, high resolution, filmless, photon imaging apparatus. The combination involves use of one or more detector plates, each being similar in form to the photon plate detector disclosed in '002, but having novel changes required to satisfy perceived product and application needs.

As in the case of the detector plate of '002, each detector plate comprises a sandwich made up of a plurality of layers comprising a first conductive layer adjacent one side of a photoconductive layer. A dielectric or non-conductive layer is disposed adjacent the other side of the photoconductive layer. On an opposite side of the non-conducting layer, a thin, at least semi-transparent second conductive layer is disposed. The detector captures a latent photonically-generated image in the form of an array of charges stored at the interface between the photoconductive and non-conducting layers. Very small area units of the charge array are converted upon readout to electric signals which are stored as an array of pixels from which a video image is created.

While each of the aforementioned factors are critical in determining overall acceptance and therefore ultimate commercial success of products based upon the invention, image processing time may have greater visibility to both patients and radiology technicians than some of the other factors. In presently known systems, a digital equivalent of image intensity of each pixel is derived by integrating an output waveform which results from exciting a pixel sized spot by a thin light beam, such as a light beam focused from a laser light source. When the light beam first stimulates a darkened area of a previously exposed detector, a portion of the detector photoconductor is excited to produce charge carriers permitting charge stored in the detector to flow to a signal-detecting circuit. The sensing period of the detected signal is dependent upon carrier mobility through the photoconductive material, which determines charge migration time through the photoconductor and effective RC time constant of the signal-detecting circuit. Migration time (t) across a photoconductor having a thickness (I) is approximated by:

$$t = I^2/MV \qquad \text{Eq. 1}$$

where M is the photoconductor's mobility constant and V is a biasing voltage across the detector. Note that the migration time increases by the square of the thickness of the photoconductor.

A novel detector plate sandwich, which is within the scope of this invention, takes advantage of thickness to migration time relationship by effectively placing two detector plates, as disclosed in '002, with a first conductive layer of one detector plate disposed adjacent a first conductive layer of the other detector plate to form a single, double-layered detector. Of course, the two first conductive layers can be a single layer of material. As one who is skilled in '002 detector construction understands, this novel detector sandwich must be read from both sides of the double-plate detector to recreate a complete image. Fortunately, each at least semitransparent layer is accessible from opposite sides of the double-layered detector for ready access by an exciting optical readout signal. Access is also provided for leads from the conductive layers to signal measuring circuits.

In a first double-layered detector embodiment, the combined first conductive layers are made sufficiently thin to pass x-rays without significant loss.

In a preferred embodiment, thickness of the two photoconductor layers combine to be substantially the same thickness as a photoconductor layer of a single-layered detector, similar to that disclosed in '002. In this manner, the same radiation absorbing power is resident in both the double-layered detector as in the single-layered detector. However, migration time of the double-layered detector is one fourth the time of migration of the single-layered detector, reducing total time to process a signal by approximately a factor of four. In this embodiment, images are derived from both sides. A final measured signal for each pixel is the sum of signals from pixels from the same coordinates of each layer.

In film based radiology, it is now well known that information related to less dense material can be derived from the shadow of more dense material by interposing a layer of aluminum or other radiation absorber between two layers of film. The film-aluminum-film layers are irradiated resulting in production of an image in each of the two film layers which, if subtracted one from the other reveals an image of material otherwise hidden in the shadow. Another embodiment of the double-layered detector involves increasing the combined thickness of the first conductive layers to selectively absorb a predetermined energy level of x-rays by means of the layer of aluminum just disclosed. In this embodiment, pixel images are derived from both sides, preferably simultaneously. The final measured signal for each pixel is the difference of signals from pixels of each layer.

As taught in '002, a single-layered detector plate may be modeled as a pair of serially connected capacitors when the detector plate is not being bombarded by photons. One capacitor, C1, comprises the first conductive layer and the surface on the other side of the photoconductive layer. A second capacitor, C2, comprises the same surface on the other side of the photoconductive layer and the thin second conductive layer. To reduce detector noise, and thereby improve detector signal-to-noise ratio, during read out, it is highly desirable to minimize the area of at least one of the conductive layers. As mentioned above, it may also be desirable to arrange the detector plate such that pixels can be readout at the same time.

For parallel operation, each second conductive layer is segmented along a line which is perpendicular to the general direction of scanning by the light source. Each segment is electrically separated from an adjacent segment by a non-conducting space. It is preferred that the non-conducting space be in the form of a thin line which is not wider than the diameter of the scanning light beam, however wider non-conducting space separation is within the scope of this invention. Such non-conducting spaces may be created in the second conductive layer either mechanically, chemically or by laser milling. When pixels are sampled in the vicinity of a non-conducting space, signals from surrounding segments are summed. As an example, when a light beam is scanned across a first segment and then over the non-conducting space between the first segment and space adjacent, such summing permits access of all pixels within the non-conducting space with minimal loss of pixel data.

Within the scope of the invention, segments may be in alignment with the direction of light scanning, but an increase in complexity and cost may make this approach less desirable. Note that, by segmenting, by simultaneously applying a plurality of precisely positioned light read-out beams, and by selectively attaching a plurality of signal detecting circuits, the stored detector image can be readout in parallel steps to reduce readout time and consequently reduce image processing time.

A further reduction in readout time can be achieved by thinning each photoconductive layer to reduce migration time. Such thinning is achieved within the scope of the invention by placing a phosphor screen over the second conductive layer while exposing the detector to image-storing radiation. Such phosphor screens are commercially available. An example of a phosphor screen capable of providing 20 lp/mm is Kodak Min-R Intensifying Screen, available from the Kodak Company of Rochester, N.Y.

If the selected phosphor screen absorbs significant radiation, photoconductive materials such as silicon may be used to replace selenium.

Note that silicon has a much higher mobility constant than selenium. Since silicon has a much higher mobility than selenium, readout time is markedly shortened. Also, a thinner A-Se layer may be used thus reducing migration time.

Even considering a combination of all of the methods for varying sensor design, it may not be possible to produce a system having a sufficiently fast image processing time by changes to the sensor plate alone. In this case, it is likely that parallel processing of pixels is necessary. As an example, if a pixel processing time is on the order of 25 microseconds and an average pixel processing period is desired to be 0.5 microseconds, about 50 pixels would have to be processed at the same time. A somewhat parallel processing detector is disclosed in U.S. Pat. Nos. 5,268,569 (Nelson et al.) and 5,340,975 (Vogelgesang) wherein the degree of parallel processing is limited by a number of stripes passed over by a single beam of light. Detector plate readout is multiplexed by scanning numbers of separate stripes in one conducting layer of a detector plate or by pulsing of the light beam as it travels cver the stripes.

However, as only one pixel can be read from any one segmented section of a sensor plate at one time, a plurality of light beams is considered the best way to speed readout beyond simple improvement in read-out speed using a single beam. Even so, achieving a high resolution image with multiple light beams is not trivial. Accuracy and constraints of precision compound structural reliability and calibration considerations.

To solve these problems, a novel multibeam light source which inherently constrains each light beam in tight tolerance relationship with all other light beams in a sensor provides an opportunity for a high speed, high resolution reader. The sensor employs a hollow opaque, cylindrical drum having a helical pattern of transparent pathways through which light is transmitted from the internal cylinder of the drum to a plane exterior to the drum.

Light is guided from a source which is disposed parallel to the exterior surface of the drum and lengthwise along the axis of the drum through a narrow portion of the exposed helical pattern. Lenses and optical stops further narrow the light beam to dispose a pattern of thin light beams projecting outward from the drum. The light beams are focused and directed to engage predetermined pixel areas on a sensor plate similar to the sensor plates disclosed heretofore.

In a preferred embodiment, the sensor plate is securely affixed to remain static while the drum is rotated and translated laterally relative to the sensor plate. In this manner each pixel of the sensor plate is read as the drum passes across the sensor plate. Relative linearity of the helical pattern provides excellent accuracy and precision of the multiple beams which are directed upon separate segments of the sensor plate. Light is pulsed from the light source to further isolate adjacent pixel areas and reduce effects of light spot smearing due to light beam motion. Also, light from the drum may preferably be directed to subtend an angle which is not orthogonal to the sensor plate and which thereby reduces scatter of the light to unexposed parts of the sensor.

In a preferred orientation, the axis of the drum, and therefore the multiple light beam alignment, is canted relative to the direction of linear motion of the drum to "orthogonalize" pixels read-from the plate sensor. Note, that if the axis of the drum is not so canted, row and column pixels will not lie in true orthogonal relationship, but by canting the drum, pixel data is made orthogonal with one coordinate of the data being parallel with drum translation. Another method for making pixel data orthogonal is by maintaining the drum axis at a different angle than the above described canted angle and varying timing of each first pulse in each line of pulses in a manner which makes the x and y data orthogonal. However, in this case, neither the x nor the y pixel data coordinates are orthogonal to direction of travel of the drum.

As mentioned, heretofore, a very important factor which affects user acceptance and is therefore of paramount importance in perceived usefulness and commercial success of a digital imaging system is image processing time for a given sensor size. A major determinant in image processing in a digital system is the number of pixels to be processed. Generally, the lower the resolution, the faster the image processing time. Often, also, the lower the targeted resolution, the greater the desired sensitivity. In a novel fashion, this invention provides a selectable, variable image processing time with variable sensitivity and resolution. Controls are provided by which optical stop width, light beam pulse width, drum translational and rotational speed, spacing between drum axis and sensor plate and angle of canting between drum and direction of drum travel are changed to-effect, in a predetermined fashion, pixel spot size and light intensity, providing a novel combination by which variable resolution, sensitivity and image processing time are profitably realized.

A primary factor which affects achieving a broad dynamic range, high sensitivity and high resolution is system noise. System noise is a statistical accumulation of noise from many sources comprising sensor plate acoustical vibration, sensor plate geometry and homogeneity variations, sensor plate capacitance, amplifier noise and gain and offset differences from amplifier to amplifier, spatial and temporal variations which produce differences in light beam intensity and light pulse rise times. Wherever possible system noise should be reduced by periodic calibration. For example, noise inherent to individual sensor plate characteristics is masked by reading a known image standard from the plate, storing the standard in a digital memory and subtracting, on a pixel by pixel basis, the standard from each processed image. Of course, whenever possible, signal should be increased relative to inherent noise to improve the signal to noise ratio. One novel method of improving the signal to noise ratio which has been determined to be surprisingly effective involves applying a reverse polarity upon a detector plate while the plate is being exposed. These and other methods and related apparatus specifically employed to improve the signal to noise ratio hereafter clearly affect resolution, sensitivity and overall system performance.

Accordingly, it is a primary object to provide a photon-based image processing system which operates without film to produce an image having a resolution in excess of 10 line pairs per millimeter.

It is a key object to provide a filmless x-ray image processing system having a resolution in excess of 20 line pairs per millimeter.

It is another key object to provide a filmless x-ray image processing system having selectably controllable resolution such that, as an example, resolution may be traded-off against image processing time when lower than maximum resolution is not required and factors controlling resolution may be varied as a trade-off for faster image development.

It is another primary object to provide a filmless photon image processing system which produces a digital replica of an image having 115 million pixels in less than 90 seconds.

It is yet another primary object to provide a filmiess photon image processing system which extracts an image from a sensor plate, pixel by pixel, by shining a beam of light upon an area from which a selected pixel is to be digitized as part of a complete image array and which processes more than one pixel at one time by shining multiple beams of light upon the sensor at the same time.

It is a fundamental object to provide a filmless photon processing system which produces images by shining concurrent multiple beams of light upon the sensor such that the accuracy of each of the multiple beams of light have an accuracy and precision of position and digitized value of each derived pixel compared with other surrounding pixels that is consistent with an image array having a resolution of 20 line pairs per millimeter.

It is a basic object to provide a filmless photon processing system having superior image producing characteristics which comprise a combination of a high resolution mode (on the order of 20 line pairs per millimeter), fast image processing (of up to 115 million pixels in less than 90 seconds) and vital sensitivity (which produces an image with lower dose than current film based systems) at a cost which is competitive with contemporary digital and film-based imaging systems.

It is an important object to provide a photoconductive sensor plate for a filmless photon processing system having two separate parallel photoconductive layers comprising stored images which are individually processed.

It is another important object to provide a layered photoconductive sensor plate for a filmless x-ray processing system having multiple parallel photoconductive layers by which measurement comparisons may be made among the layers to images subtracted one from another to produce differential images from which high energy pixel components have been expunged.

It is still another important object to provide a filmless x-ray processing system which produces images from a low cost single sensor plate comprising multiple conductive layers.

These and other objects and features of the present invention will be apparent from the detailed description taken with reference to accompanying drawings.

BRIEF DESCRIPTION OF THE DRAWINGS

FIG. 1 is a cross section of a layered sensor plate disclosed in earlier related art.

FIG. 2 is a cross section of a layered sensor plate similar to the plate seen in FIG. 1, but having one layer segmented.

FIG. 3 is a cross section of a layered sensor plate similar to the plate seen in FIG. 2, but comprising an additional layer disposed above the segmented layer.

FIG. 4 is a cross section of a layered sensor plate having two photoconductive layers separated by a centrally disposed conductive layer.

FIG. 5 is a cross section of a sensor plate similar in construction to the double photoconductive layered sensor plate seen in FIG. 4, but having a pair of centrally disposed conductive layers separated by a middle non-conducting layer.

FIG. 20 is a schematic diagram showing the shape of a pixel area scanned by the drum scan tube seen in FIGS. 18 and 19.

FIG. 21 is an exploded perspective of the drum scan tube of FIG. 18.

FIG. 22 is a cross section of a segment of an assembled cylindrical scan tube and associated optics.

DETAILED DESCRIPTION OF THE ILLUSTRATED EMBODIMENTS

Figure 13:
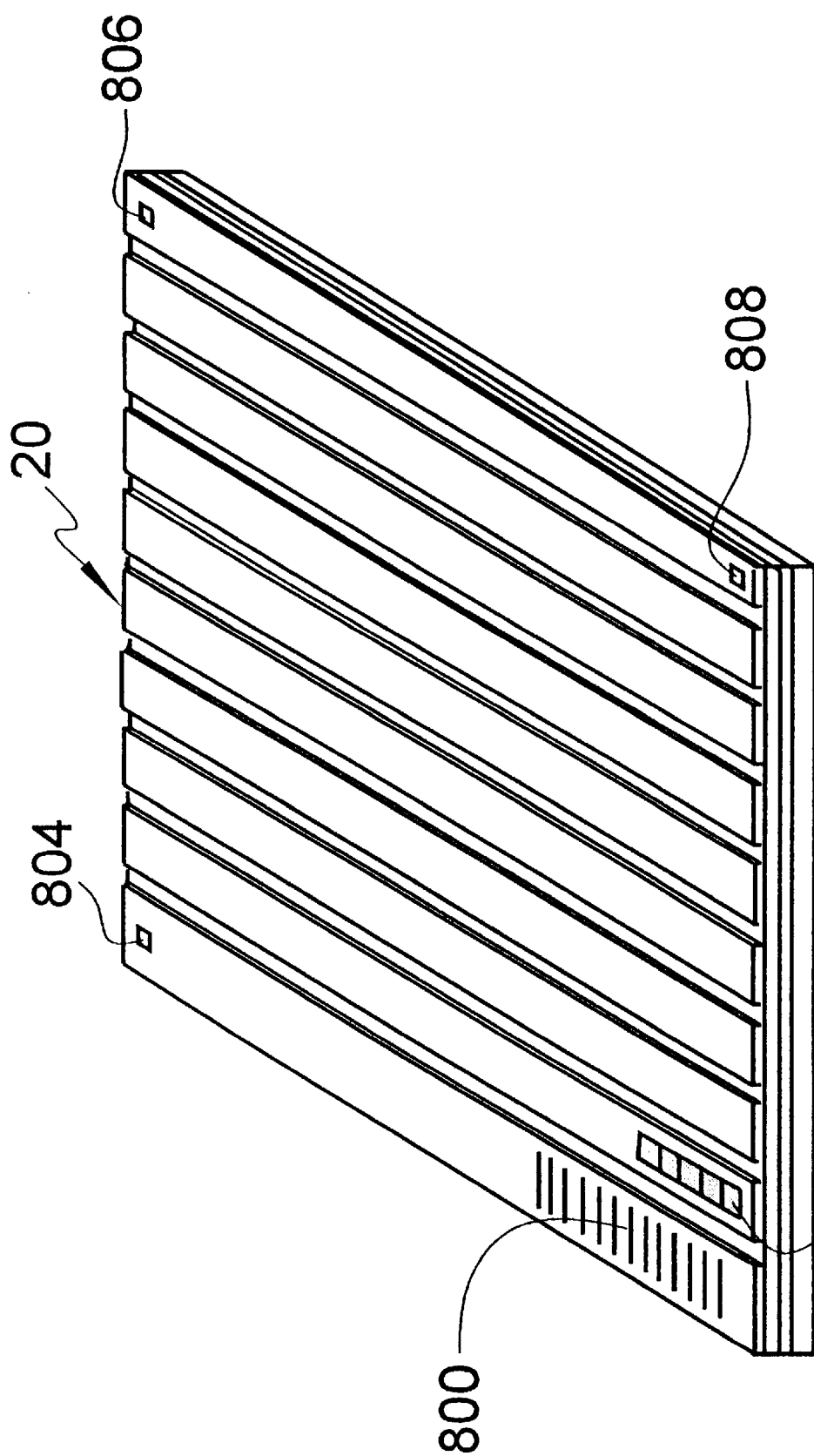
FIG. 13 is a schematic representation of a sensor plate whereupon calibration and plate identification are disposed.
Figure 14:
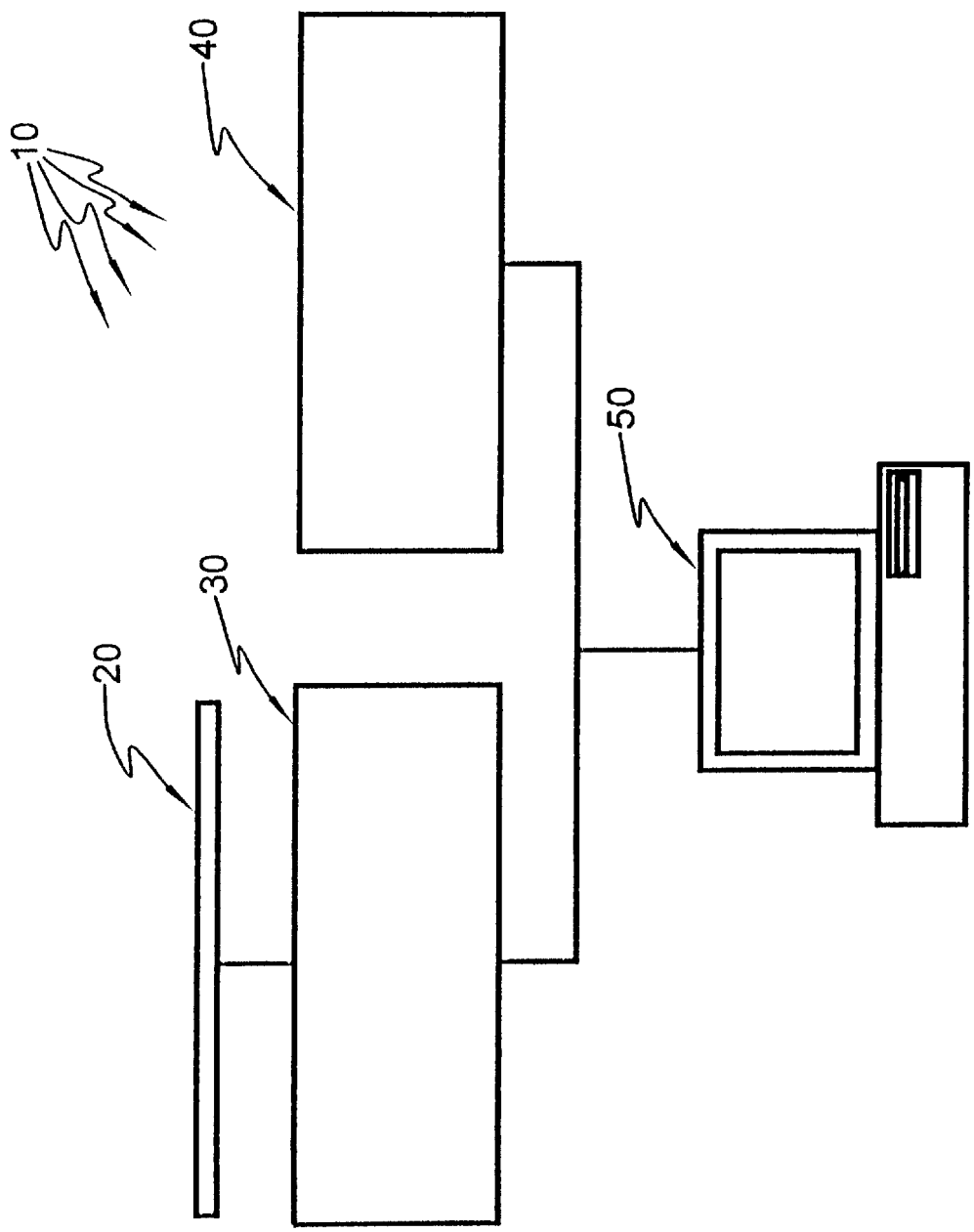
FIG. 14 is a block diagram of a digital image processing system which processes images from sensor plates such as those seen in FIGS. 1–5.

In this description, the term proximal is used to indicate the segment of the device normally closest to the object of the sentence describing its position. The term distal refers to the other end of the device. Reference is now made to the embodiments illustrated in FIGS. 1–29 wherein like numerals are used to designate like parts throughout. Central to a filmless digital photon image processing system which has the attributes of high resolution, rapid image processing time, high sensitivity and low cost with a broad or high dynamic range is innovative layered photon plate sensor technology, exemplary embodiments of which are seen in FIGS. 1–5. However, sensor technology alone does not assure those attributes. Other elements which are part of a system 10 seen in block diagram form in FIG. 14 must all be usefully combined for that purpose. As seen in FIG. 14, system 10 comprises a sensor plate (which may be of various forms as seen in FIGS. 1–5 and is generally designated by the numeral 20), a scanning system 30, signal processing electronics 40 and a computer controller and image processor 50.

Interactive structural and electrical interfaces between elements of system 10 are disclosed in detail hereafter, but first, attention is directed toward innovative elements of sensor plate 20. Reference is now made to FIG. 1 which is a cross section of a sensor plate previously disclosed in prior art such as '002. In FIG. 1, sensor plate 20 comprises a layered configuration 100. Configuration 100 comprises, in seriatim, a superiorly disposed (top) conducting layer 102, an insulating layer 104, a photoconductive layer 106 and an inferiorly disposed conductive layer 108. Generally, there is a blocking layer interposed between photoconductive layer 106 and conductive layer 108, but such is not shown in FIGS. 1–5 as the photoconductive material of layer 108 is often made from aluminum which inherently comprises an aluminum oxide layer which performs as the blocking layer.

Although other materials may be used, present preferences are indium tin oxide (ITO) for layer 102 and polymer for layer 104. Amorphous selenium is preferred for most sensor applications for layer 106, although, in some cases, amorphous silicon or other photoconductive material may be used. As mentioned above, aluminum is commonly used for layer 108. Of major importance in selecting materials for layers 102 and 104 is assurance of optical photon transmissivity. It is especially important when amorphous selenium is used in layer 106 that layers 102 and 104 are relatively transparent to light having a wavelength in the range of 400–500 nanometers.

Figure 2A:
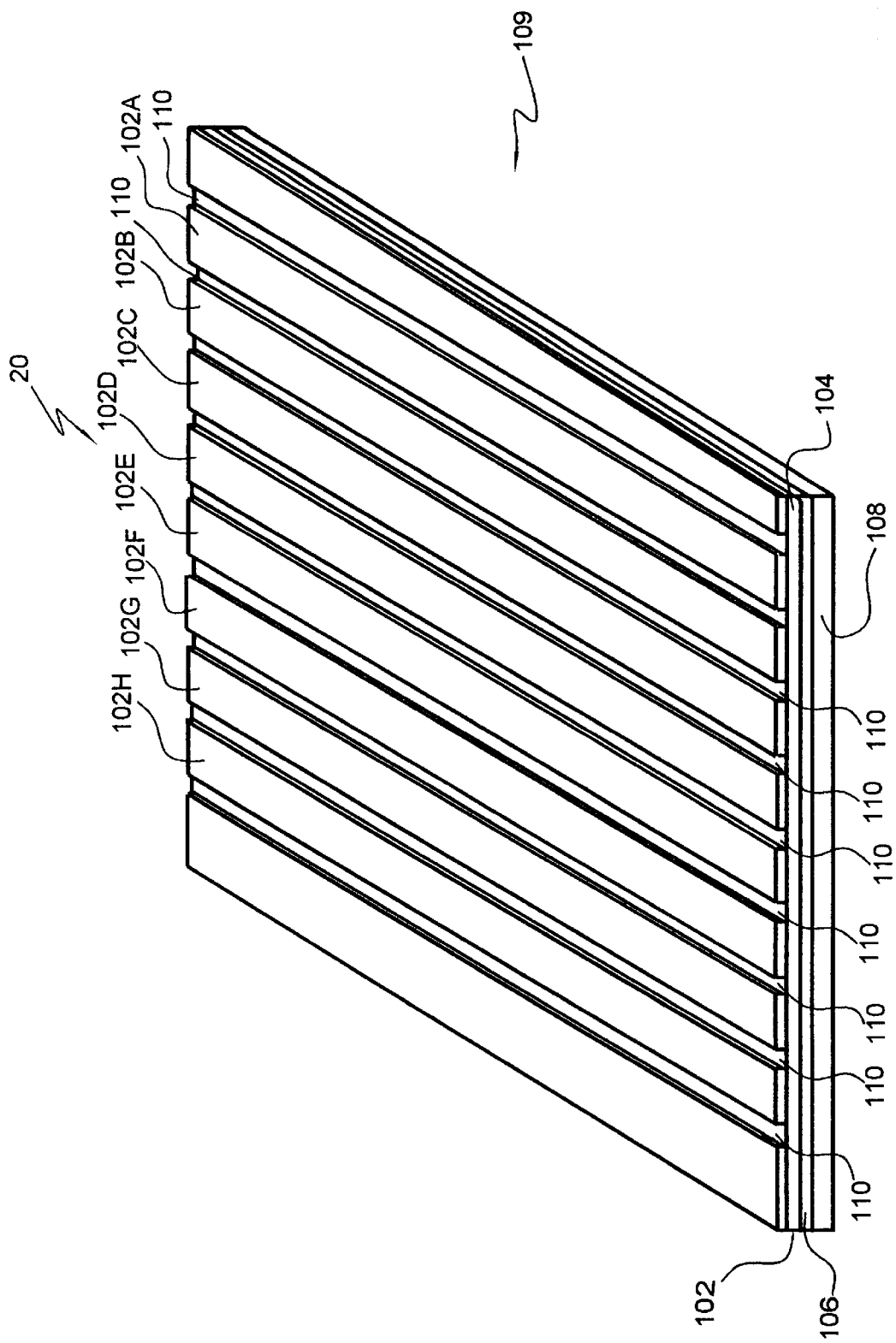
FIG. 2A is a perspective representation of an imaging portion of the segmented sensor plate of FIG. 2.

As clearly disclosed in '002, one of the major deterrents to high sensitivity is a low signal to noise ratio which is affected in part by capacitance of sensor plate 20. A primary method for reducing effective capacitance of sensor plate 20 is accomplished by segmenting one of the conductive layers into a plurality of electrically isolated conductive areas or strips. An example of such segmentation is seen in configuration 109 in FIGS. 2 and 2A. In FIG. 2A, note that layer 102 is divided into eight separate image-producing segments, 102A–H. It should also be noted that division of layer 102 into eight segments is for example only and layer 102 may be divided into various numbers of segments as desired and as is disclosed hereafter.

Electrical isolation of each segment from other segments not only reduces capacitance, but permits each individual segment to be accessed separately from the others for readout. Such separate access allows different segments to be sampled and individual pixels to be processed at the same time, thereby providing an opportunity for parallel or concurrent readout from a plurality of segments or strips simultaneously to reduce image processing time. For such purposes, each segment 102A–H is connected to a signal processing circuit which functions to filter and amplify electrical signals emanating from that segment.

Segments 102A–H are separated by spaces, generally numbered 110. Width of spaces 110 between segments 102A–H should be wide enough for electrical isolation, but narrow enough for charge carriers to electrically influence with one or both segments adjacent to affected segment 110. It is preferred that width of spaces 110 be in the range of 5–20 microns, although other widths may be used within the scope of the invention.

Referring to FIG. 2, note that superior to layer 102 is a transparent protective layer 112. Of course, layer 112 must be sufficiently non-conductive to provide electrical isolation for each segment 102A–H. It is also preferred that layer 112 be applied as a liquid to permit spaces 110 to be filled. Layer 112 should also be of sufficient hardness to act as a protective layer for layer 102. In addition, layer 112 may be used to provide an hermetic seal and as an anti-reflective coating. Materials which can be used for layer 112 are commercially available and well known in the electrical insulator and optics art. It is also preferable to provide an anti-reflective layer (not shown) between layers 106 and 104.

U.S. Pat. No. 4,763,002 ('002), issued in 1988, discloses a phosphor screen layer (not shown) interposed between an ITO layer (such as layer 102) and a selenium layer (such as layer 106). A different and novel use of a phosphor screen is seen as part of configuration 113 in FIG. 3 wherein a phosphor screen 114 is disposed above a superior transparent insulating layer, such as layer 112. Note, that in this manner, phosphor screen 114 may be used in particular when extra sensitivity is desired. Further, phosphor screens having different mesh sizes may be used to achieve distinct resolution characteristics for different imaging purposes. In x-ray applications, use of such a screen 114 can reduce dose to a patient. Such phosphor screens are available in the film-based x-ray image processing art. Care must be taken in selecting screens as resolution is limited by screen mesh size and the screen preferably should have luminescence in the range of 400–500 nanometers (the range where selenium is most sensitive). An additional advantage of phosphor screen 114 use is an opportunity to reduce the thickness of photoconductive layer 106. As an example, for selenium, layer 106 may be reduced by a factor of 10 through the use of a screen 114. Such reduction would decrease charge transport time within the photoconductive layer and, in this example, would reduce image processing time by a factor of 100. Screen 114 also provides an opportunity to use a material different from amorphous selenium such as amorphous silicon which, due to more rapid migration time in silicon, yields a still more rapid image processing time. In all cases, screen 114 should be removed when reading an image from sensor plate 20.

Novel examples of double layered photon sensor plates configurations, from which two images of the same object are recorded simultaneously, are seen in FIGS. 4 and 5. In FIG. 4, a configuration 120 comprises, in seriatim, a superior insulating layer 112, a segmented conductive layer 102, a non-conducting layer 104, a photoconducting layer 106 and a conducting layer 108. Then, in mirror image orientation, configuration 120 further comprises another photoconductive layer 106', another non-conducting layer 104', another segmented conducting layer 102' and an inferior insulating layer 112'. Note that segmenting of layers 102 and 102' provide image processing and signal to noise advantages, but that layers 102 and 102' may also be non-segmented within the scope of the invention. Similarly, utilizing layers 112 and 112' offers advantages, as described heretofore, but use of such is not necessary within the scope of sensor plate inventions.

One novel application of configuration 120 is provided by making layer 108 sufficiently thick to filter lower energy radiation from that half of the sensor plate away from the x-ray radiation source. As an example, it is standard practice in film based x-ray imaging to use an aluminum sheet, interposed between two film layers, as a filter to shield film against unwanted radiation. In configuration 120, layer 108, is sufficiently thick to be a filter to deprive layers distal to the x-ray receiving surface from low energy radiation. In this manner, radiation reaching the distal layers is purged of low energy photons (x-rays). Thus, a resultant x-ray image captured in distal photoconductive layer 106' is generally from soft tissue areas where x-rays meet minor attenuation while passing through a subject being x-rayed. Note, that by taking a difference between top and bottom images, high energy images are subtracted revealing an image of lower energy absorbing structures otherwise hidden in the shadow of higher energy absorbing structures. Of course, layer 108 may be made from a sandwich of a plurality of materials.

As is apparent to those familiar with dual energy film image processing, to guard against artifacts, care must be taken to match on a pixel to pixel basis calculations which produce a differential image. Dual energy imaging is particularly applicable to mammography wherein an image captured in bottom photoconductive layer 106 comprises skin and soft tissue and an image captured in top photoconductive layer 106' records anomalies such as calcification. In the case where layer 108 is too thin to provide structural support for configuration 120, it is advisable to mount configuration 120 upon a clear glass or other material substrate for structural stability. Having the facility of a dual plate permits a differential image to be captured with a single x-ray exposure eliminating double x-ray exposure procedures necessary with single layer receptors. Such facility also eliminates problems related to patient movement between procedures requiring double exposure steps.

In configuration 130, sensor plate 20 is seen to comprise, in seriatim from superiorly disposed to inferiorly disposed position in FIG. 5, an insulating layer 112, a segmented conductive layer 102, a non-conducting layer 104, a photoconducting layer 106, a relatively thin conducting layer 108 and an x-ray transparent layer 132. Then, in mirror image orientation, configuration 130 further comprises another photoconductive layer 106', another non-conducting layer 104', another segmented conducting layer 102' and an inferior insulating layer 112'.

In one application, the combined thickness and therefore the photon image capture capacity of layers 106 and 106' in FIG. 5 is the same as, for example, thickness of layer 106 of FIG. 2. Since charge migration time is a function of the square of the thickness of a photoconductor (see Eq. 1), each pixel of an image can be processed (read) from configuration 130 at four times the rate (one-fourth the time) as a pixel of an image processed from configuration 109. As configuration 130 is symmetrical about a center line drawn through layer 132, use of configuration 130 is the same when upright or inverted. When configuration 130 is used as a higher speed image processing sensor plate, layers 108 and 108' should be sufficiently thin to pass x-rays without marked degradation. To produce a complete image in this application, digital data derived from each of the two pixels having the same planar coordinate are summed to provide a final digitized value for the pixel to be displayed for that coordinate.

The interrelated factors of resolution, sensitivity and dynamic range are all affected by the effective noise inherent in all elements of an image acquisition and processing system, such as system 10. Of primary concern are the elements associated with sensor plate 20. Reference is now made to FIGS. 6–9 wherein a sequence of voltage application steps related to various stages of image acquisition are seen. For purposes of example, sensor plate configuration 100 is depicted in FIGS. 6–9, although other sensor plates being similar in form and function to configurations seen in FIGS. 1–5 may be processed using steps outlined herebelow. The steps are similar to steps disclosed in '591, except for an innovative change clearly disclosed hereafter.

Figure 6:
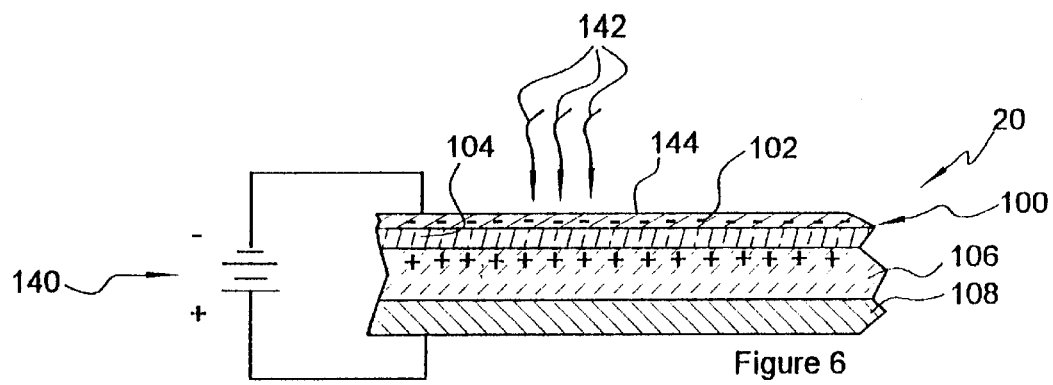
FIG. 6 is a schematic representation of application of voltage across conductive layers of a sensor plate while the sensor plate is being charged.

Application of a D.C. voltage (depicted by battery 140) and light (depicted by lines and arrows 142) for erasing and cleansing sensor plate 20 of previously stored images and, thereby, preparing plate 20 to store a next image is seen in FIG. 6. To erase a previous image, battery 140 is connected across superior conducting layer 102 and inferior conducting layer 108. Simultaneously, superior surface 144 of layer 102 is exposed to an ultraviolet light 142. Light 142 causes photoconductive layer to transport positive charges from conductive layer 108 at the same time while photoconductive layer 102 is being negatively charged. Periodically, it is considered expedient to bath sensor plate 20 at an elevated temperature of 140 degrees Farenheit while disposed in a dark environment to relax the plate and eliminate trapped charges.

Figure 7:
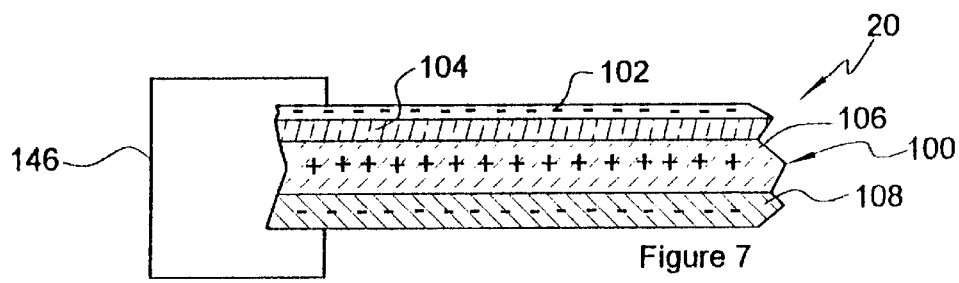
FIG. 7 is a schematic representation of a step during which the conductive layers are shorted before exposing the sensor plate to photon radiation to record an image on the plate.

Once sensor plate 20 is fully charged, both light 142 and voltage from battery 140 are removed. From this point, until an image has been read from sensor plate 20, after exposure to a target object, sensor plate 20 must be protected from exposure to spurious or ambient light. With light 142 removed, photoconductive layer 106 becomes nonconductive retaining the positive charge. As a next step, conductive layer 102 is electrically shorted to conductive layer 108 by a conductive line 146, which distributes negative charge between conductive layers 102 and 108, as seen in FIG. 7.

Figure 8:
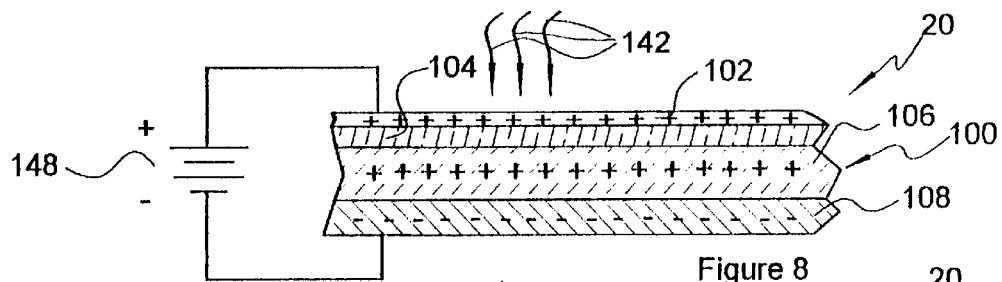
FIG. 8 is a schematic representation of application of a reverse bias voltage during exposure of image-producing radiation upon the sensor plate.

Sensor plate is now ready for exposure to the target object. If sensor plate 20 is used to record x-ray images, the plate may be disposed in place of film in an x-ray apparatus. As seen in FIG. 8, a reverse D.C. voltage bias (depicted by battery 148) is applied across conductive layers 102 and 108. The preferred reverse bias voltage is on the order of 150 to 3000 volts and provides an external field assisted discharge decreasing susceptability to electron hole pair recombination. Surprisingly, this reverse bias increases each signal read from sensor plate 20 by a factor which increases signal to noise ratio by about a factor of four over signals read from plates without the reverse bias, thereby increasing sensitivity and improving the opportunity for higher resolution and broader dynamic range. As clearly disclosed in '591, exposure of sensor plate 20 to x-rays or other photons, records an image in the form of an array of selectively stored charge in photoconductive layer 106. After exposure, conductive layer 102 may be electrically shorted to conductive layer 108 as seen in FIG. 7.

Figure 9:
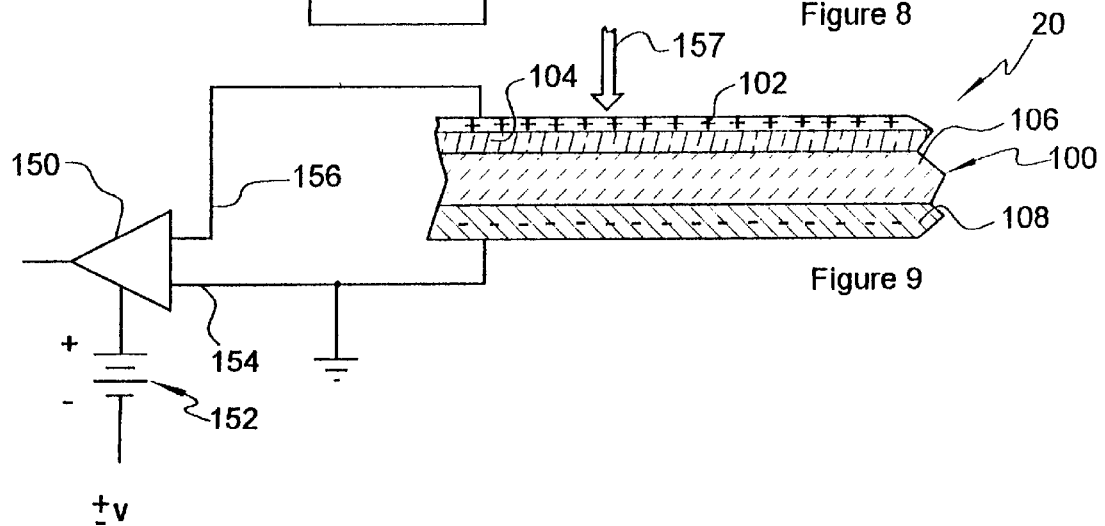
FIG. 9 is a schematic representation of a single amplifier and bias voltage being connected to the sensor plate while a light beam is selectively traced across the plate to excite, on a pixel by pixel basis, discrete areas of the plate to thereby read a previously recorded image from the plate.

The stored image is then read from sensor photoconductive layer 106 by affixing at least one amplifier, designated 150, to conductive layers 102 and 108 as seen in FIG. 9. As is the case in the step seen in FIG. 8, a D.C voltage, depicted as an optional battery 152 having an output of a potential preferably in the range of 1200 volts (although other voltages ranging from 150 volts and higher may be used), is applied as a reverse bias to an amplifier 150. Details of preferred design of amplifier 150 are provided hereafter. A first amplifier input 154 is connected both to a reference ground and to layer 108. A second input 156 to amplifier 150 is connected to conductive layer 102. Systematically a light beam, symbolized by arrow 157, is used to selectively illuminate each pixel of the image, stored in layer 106, through layer 102.

For improved image processing time, one of the conductive layers (102 or 108) may be segmented and multiple beams of light simultaneously used to read pixel information from sensor plate 20 in parallel. For double layered sensors, such as configurations 120 and 130, comments related to layer 102 also apply to layer 102', as well. Similarly, comments related to layer 106 apply to layer 106', as well, when layer 106' is an element of a configuration.

Figure 10:
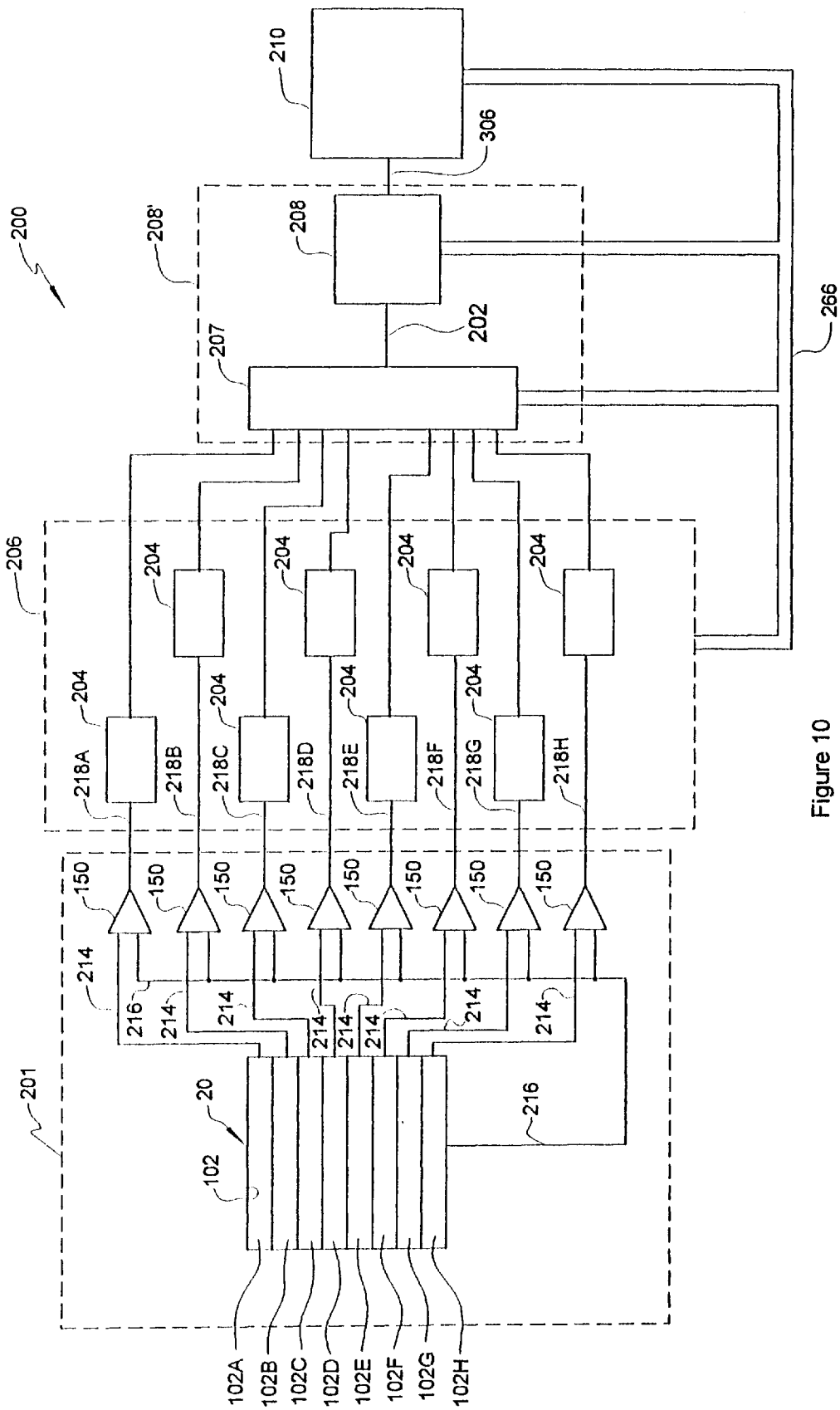
FIG. 10 is a block diagram of a pixel sensing circuit used to detect and digitize data read from the sensor plate.

A block diagram of an exemplary image processing system 200 which performs as signal processing electronics 30 (see FIG. 14) in pixel acquisition is seen in FIG. 10. Image processing system 200 comprises a sensor plate 20 (enclosed by dashed line box 201), a plurality of signal conditioning circuits 204 (enclosed by dashed line box 206), a multiplexing circuit 207, an analog-to-digital (A/D) conversion subsystem 208 and an image processor and controller 210. While numerous other processors are available and may be used within the scope of the invention, Intel processor 8051 is an example of a processor which may be used.

It is preferred that sensor plate 20 comprise an isolating preamplifier 150 for each segment (102A, 102B, etc.) into which layer 102 (and 102') is segmented. Each preamplifier 150 is preferably located in close proximity to the segment to which it is connected. As seen in block diagram form in FIG. 11, preamplifier 150 comprises a pair of input leads (214,216) and an output lead (generally numbered 218), one input lead 214 being connected to a segment (102A, 102B, etc.) and the other input lead 216 being commonly connected to layer 108 (or, in the case of a double layered plate, one input lead 214 of a preamplifier 150 connected to a segment of 102' and the other lead 216 being connected commonly to layer 108'). Each output lead 218 is connected to a signal conditioning circuit 204. To clarify connection of each lead 218 with circuit 204, output leads 218 are alphanumerically sequenced as 218A–H (see FIG. 10) to correspond with segments 102A–H from which signals are respectively initiated.

Alternatively, each preamplifier 150 may be disposed off plate 20, but due consideration must be given to the degree noise is increased due to extended lead length and connector noise and the consequential that affect upon system performance.

Figure 11:
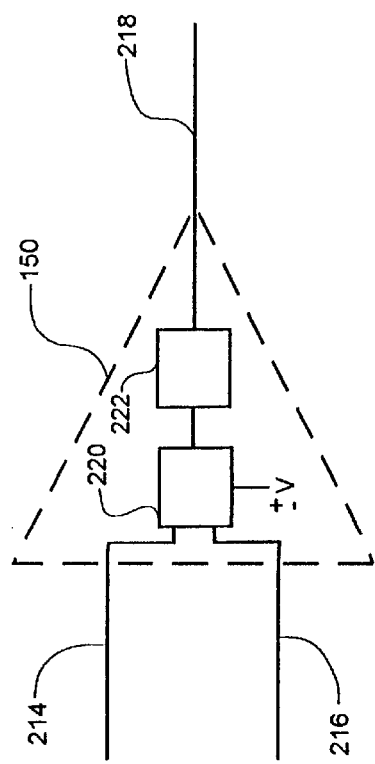
FIG. 11 is a block diagram representation of a single preamplifier of the pixel sensing circuit of FIG. 10.

As seen in FIG. 11, circuit 150 is comprised of a bias-isolation circuit segment 220 serially connected to a low noise buffer amplifier. As seen in FIG. 9, a bias from a voltage source 152 is applied to segment 220 thereby providing a bias which may range from −2000 to +2000 volts. Segment 220 should provide an input impedance in the range of 100 megohms, although lower impedances may be used when lower signal-to-noise ratios are acceptable.

Inherent noise of buffer amplifier 222 should be less than 10 nanovolts * $(Hz)^{-\frac{1}{2}}$ at 10,000 Hertz. Amplifier 222 should have a gain bandwidth of greater than 500,000 Hertz and a realtively high input impedance in the range of 45,000 ohms. Such input impedance is achievable through use of field effect transistors. Also amplifier 222 should be over-voltage protected. Design of circuits 220 and 222 is well within the current state-of-the-art of those persons skilled in contemporary electronic circuit design and can be accomplished without undue experimentation. Preamplifier 150 preferably employs a single integrated component, however a multi-component amplifier, such as EG&G 142B may be used.

Figure 12:
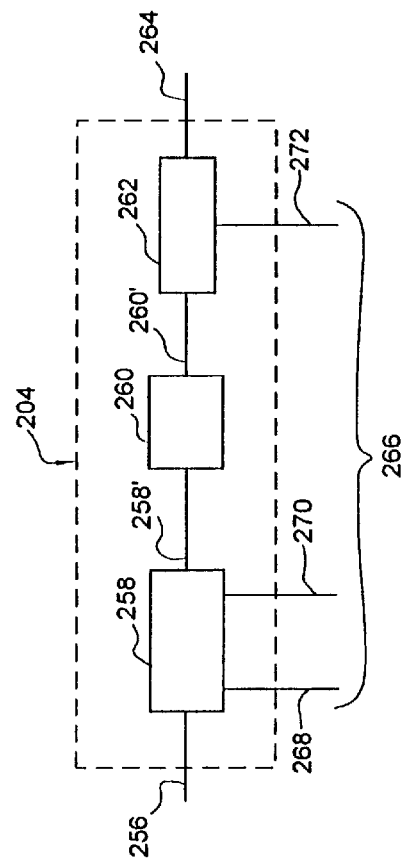
FIG. 12 is a schematic representation of a signal conditioning circuit.
Figure 28:
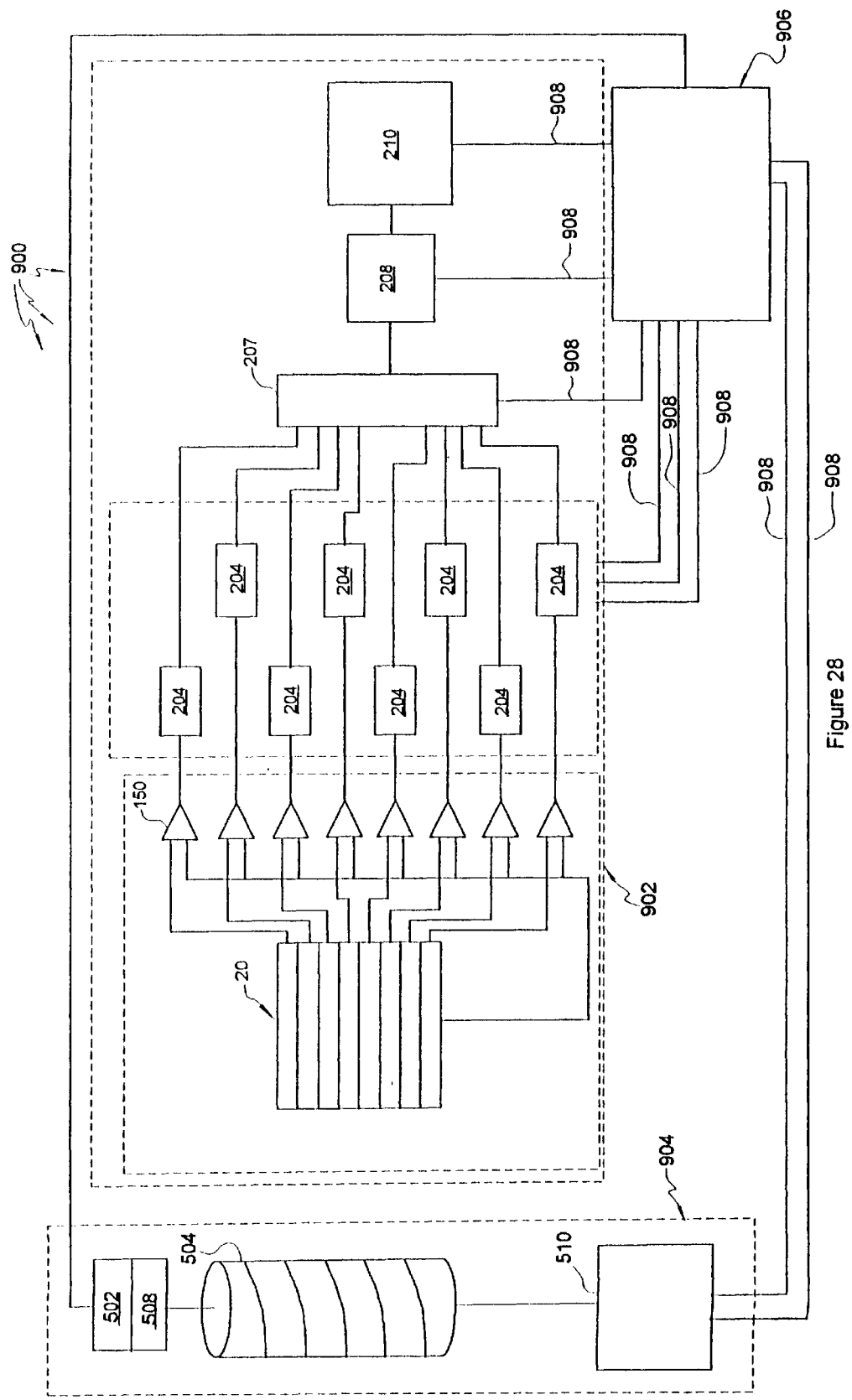
FIG. 28 is a block diagram representing an image acquisition system including a pixel sensing circuit similar to the circuit seen in FIG. 10, a mechanical portion as represented in FIG. 17 and a central processor.

Referring again to FIG. 10, signals are communicated from plate via lines 218A–H, each of which is inidvidually connected to a signal conditioning circuit 204. Reference is now made to FIG. 12 wherein a block diagram of an individual signal conditioning circuit 204 is seen. Each circuit 150 output lead, e.g. lead 218, is connected as an input lead 256 of a circuit 204 for amplifying and processing of a signal from plate 20 as disclosed hereafter, although other methods of signal processing may be used within the scope of the invention. As seen in FIG. 12, an electrical signal received on lead 256 is serially processed through an amplifier/integrator circuit 258, a final amplifying stage 260 and a sample and hold circuit 262. A filtered, amplified and peak integrated value of an incoming signal is transmitted for ultimate analog-to-digital conversion through an output lead 264. Timing and control is performed by a digital processor and controller, such as image processor 210, seen in FIG. 10. However, it may be preferrable to utilize a second controller as seen in FIG. 28 (processor 906), as a central control processor. More detail on use and integration of a second controller is provided hereafter. A plurality (bundle) of control lines, generally seen as double lines 266 in FIG. 10, provides control signals to each signal conditioning circuit 204, multiplexing circuit 207 and analog-to-digital converter 208.

Amplifier/integrator circuit 258 (see FIG. 12) receives a signal via line 256 for amplification and integration. It is also preferrable to provide a filter in conjunction with circuit 258, band-passing frequencies from 200 to 100,000 Hertz. Currently, it is preferred that amplifier/integrator circuit 258 have the following characteristics:

1. An input range of ±10 millivolts.
2. A low input impedence (z) and referenced to virtual ground.
3. An integration time of less than 20 microseconds.
4. An integration slew rate greater than 1 volt per microsecond.
5. A reset slew rate greater than 1 volt per microsecond.
6. An output range of ±1 volt.
7. A non-linearity of ±0.005% over the full scale amplifier range.
8. Integration droop rate of less than 5 nanovolts per microsecond.
9. Output noise of less than 1.0 microvolt$_{rms}$.
10. An integration capacitance of 1 to 10 picofarads.

Generally, an analog value for an individual pixel which is amplified and presented to circuit 258 has a transitory voltage having a period of less than 25 microseconds. Amplifier/integrator circuit 258 integrates the analog signal to reduce noise and increase signal amplitude. Each circuit 258 comprises a pair of control lines 268 and 270, which are a part of bundle 266. Control line 268 is a gating control line which controls each integration period. Control line 270 is another gating control line which causes circuit 258 to dump a last integrated pixel signal in preparation for integrating a subsequent pixel signal.

Final amplifying stage 260 receives input from data line 258'. Preferably, the gain of circuit 260 is in the range of 50 from 0 Hz to 100 KHz. In any event care should be taken when establishing DC gain of circuit 260 to assure circuit 260 does not saturate at maximum output of circuit 258. Output noise of stage 260 should be less than 0.25 mv. Stage 260 linearity should be better than 0.005% of full scale range of the stage. Slew rate should be at least one volt/microsecond.

Sample and hold circuit 262 is gated by another control line 272 of bundle 266 to capture a representative pixel sample of an integrated and amplified signal from circuits 258 and 260 through lead 260' and hold the signal until digitized for ultimate storage as a digital representation of the pixel. Preferably, circuit 262 has the following preferred characteristics:

1. Unity gain.
2. Hold droop rate: 0.5 microvolts/microsecond.
3. Non-linearity: less than an equivalent of ± one-half the least significant analog-to-digital conversion bit over full scale range of amplifier 260.
4. Output noise limit: less than an equivalent of ± one-half the least significant analog-to-digital conversion bit over full scall range of amplifier 260.
5. Sampling slew rate: 200 volts/microsecond.
6. Sample pules period: 0.1 to 1 microsecond.
7. Offset voltage: ±½ least significant bit value of A/D converter.
8. Gain error: ±½ least significant bit value of A/D converter.
9. Acquisition time: 200 nanoseconds.

Components and associated circuitry for circuits 258, 260 and 262 are well known and commercially available. Sample and hold circuits are presently available on a single integrated circuit chip, such as National Semiconductor part LF398.

Analog switches in multiplexing circuit 207 must operate at relatively high speeds (in microseconds or fractions of microseconds). High speed analog switches are preferred. As an example, an Analog Devices ADG333A integrated circuit may be used if circuit 207 is designed as a separate part.

In the current art, there are many integrated circuits which can fulfill requirements for A/D subsystem 208. To reduce cost, it is often preferable to time-share a single A/D converter to process signals from more than one multiplexer 207 output. An example of an eight channel data acquisition system is Analog Devices AD7891 which comprises a multiplexer (which can be used to perform the switching functions of multiplexing circuit 207), a track/hold amplifier and a converter block and is symbolized by dash-line-enclosed block 208'. Binary signals, which in combination transmit the value of digitally converted analog pixel signal from block 208', are sent to processor 210 via leads 306 as seen in FIG. 10.

In summary, at least one electrical signal for each sampled pixel is generated as the area where the pixel resides is illuminated. If the pixel area resides in a region where there is a space 110 between two plate segments (such as segments 102A and 102B) signals emanating from segments surrounding space 110 must be summed. However, each electrical signal is preferably first amplified via a preamplifier 150 to reduce susceptibility to noise and then filtered, amplified and digitized through circuits 204 and 208' and finally stored as a numeric representation of image pixel value in processor 210. A/D converter 208 converts the signal to binary format for ultimate storage as part of an image array in processor 210 which receives parallel input of the binary signals from A/D subsystem 208'. Each pixel is mapped into coordinates which represent its position in the geometry of the sampled image. When the pixel area resides between two plate segments, digitized signals from each segment surround the associated space are summed in processor 210 to form the numeric representation of that pixel.

Figure 15:
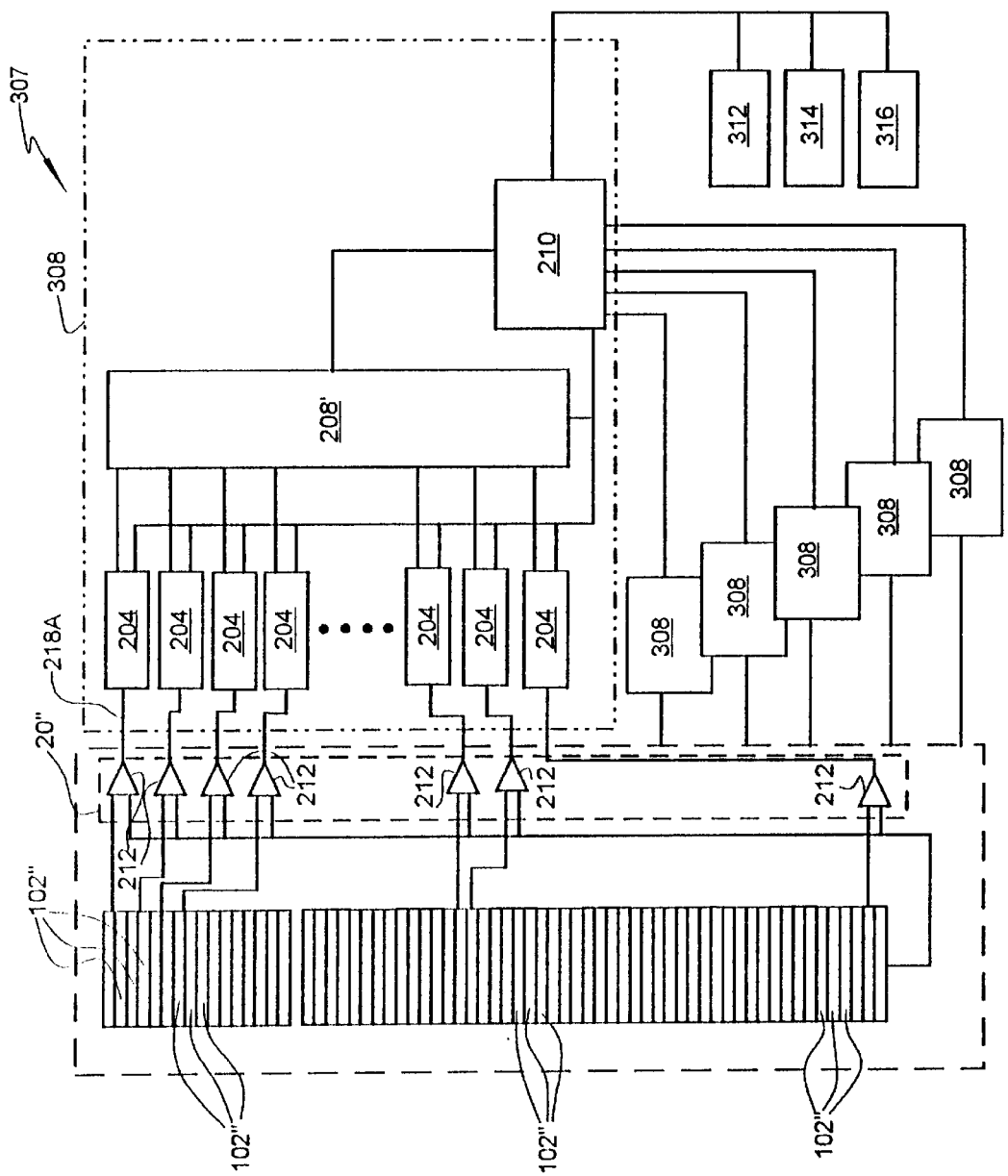
FIG. 15 is a block diagram of a pixel sensing circuit subsystem which is an extension of the circuit block diagrammed in FIG. 10.

In the block diagram of FIG. 10, a sensor plate 20 is exemplarily portrayed as an eight segment sensor plate. It is more likely that layer 102 of a sensor plate, such as plate 20" in FIG. 15, is segmented into many more segments than plate 20 of FIG. 10 and may comprise thirty or more segments, generally numbered 102", in a larger system, such as system 307 of FIG. 15. System 307 is better suited to image sizes for commercial applications, such as sizes required for mammography applications than a system having fewer plate 20 segments, such as system 200.

Similar to the block diagram of FIG. 10, each segment of sensor plate 20" is connected to a preamplifier 150, from which signal leads, of which lead 218A is an example, are connected to a signal conditioning circuit 204. The number of segments of sensor plate 20" is determined by the effective image capturing linear dimension in the direction of light scan progression across plate 20", a value of plate capacitance desired and the predetermined number of parallel channels to be read simultaneously to achieve a predetermined total overall image processing time. To a lessor extent, the number of segments is determined by parts cost, e.g. number of time-shared A/D converters, switches, amplifiers, etc. As an example, consider an imaging portion of a plate 20" having a linear dimension of eight inches (approximately 200 millimeters), a resolution of 20 line pairs/millimeter (lp/mm) and one hundred twenty eight pixels being desired per segment. In this case, each segment is 6.4 mm wide and about sixty-two segments are required in plate 20. The sixty-two segments require sixty-two preamplifiers 150 and sixty-two circuits 204.

As presently preferred, each signal conditioning circuit 204 is connected to an input lead of a multiplexed A/D converter, such as A/D subsystem 208'. For sixty-two signal conditioning circuits 204, six time sharing A/D subsystems 208' are presently required. Gating control and digital signal processing for data analog to digital converted by A/D converter block 208' is provided by one processor 210.

In FIG. 15, a dashed line block 308 encloses that set of electrical circuits, which comprise associated signal conditioning circuits 204, a single A/D subsystem 208' and a processor 210. Five other blocks 308 are seen in FIG. 15, providing for up to sixty-two segment multiplexing. Each block 308 comprises the same parts and performs the same function. As those who are familiar with the art of digital system programming and use understand, unused (extra) A/D converter channels may be employed for other purposes such as self-test and system status determining functions.

Outputs from each circuit block 308 is delivered to a high speed computer processor 210. When the number of parallel operations exceeds the capacity of a single processor 210, multiple processors are used. Another processor, not shown in FIG. 15, may be used to receive and steer images to viewing screens, digital storage, printing and through communications for remote viewing for practical use away from the site of image acquisition. Optional peripherals which may be added are printers and film printers 312, video displays 314, a large capacity image storage medium 316 (which may be a write/read CD player) and a communications network interface (such as that for a Dicom Net). Of course, other circuit configurations may be used within the scope of the invention. It is important to note the transition from production of film images to storage of images upon computer disks as part of CD player 316 network. This transition has a profound impact upon overall radiographic operational costs, both in eliminating cost of film and in film storage and. accessing.

Figure 16:
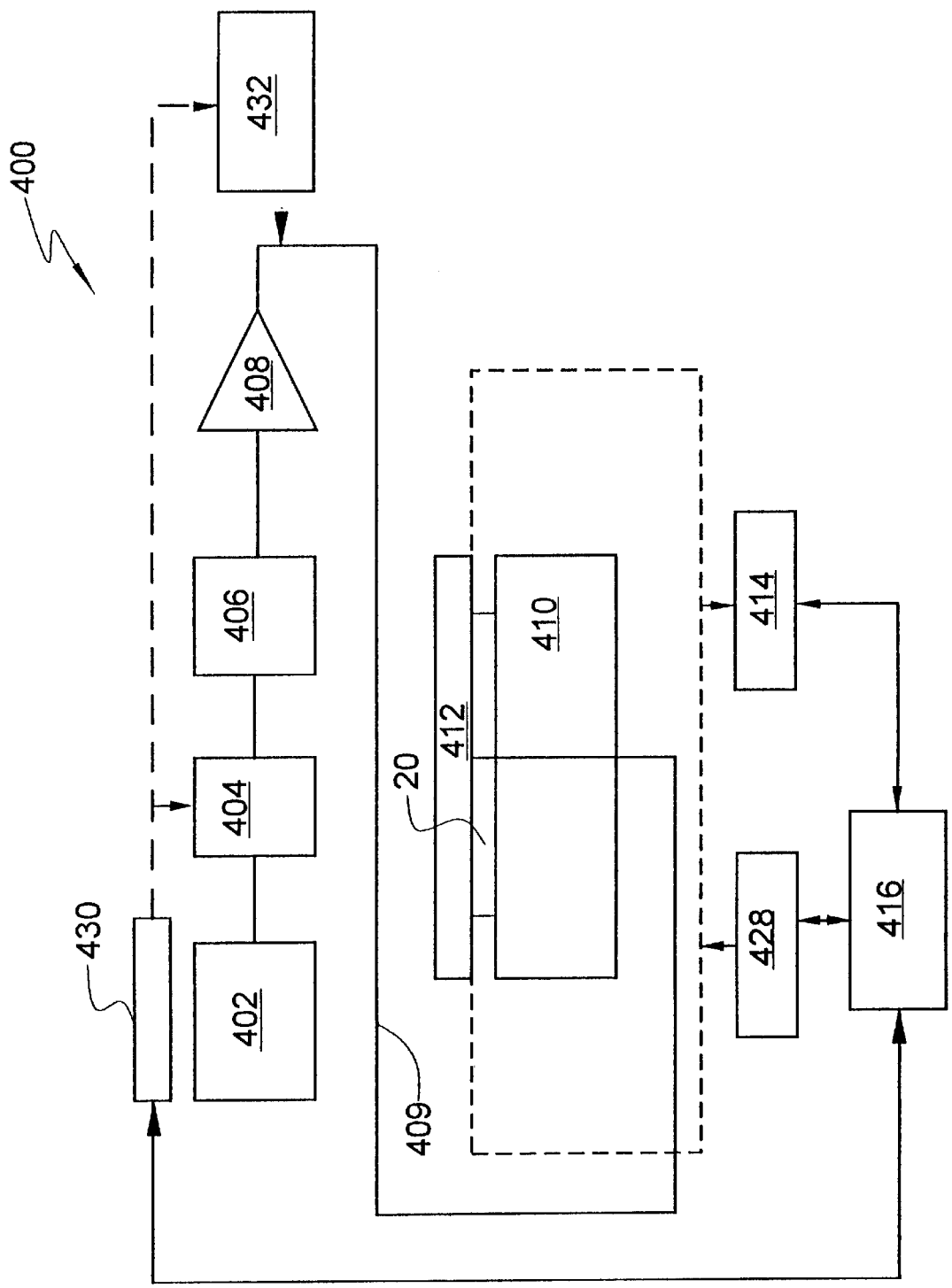
FIG. 16 is a block diagram of a demonstration test unit used to demonstrate high resolution image processing from a digital plate.

During 1996, a prototype x-ray imaging system was fabricated for the purposes of assessing resolution and segmentation parameters when deriving images from a sensor plate 20. A block diagram of the prototype x-ray imaging system, numbered 400, is seen in FIG. 16. System 400 comprised a laser 402, a modulator 404, an optics subassembly 406 and a fiber optic interface 408 and fiber optic cable 409 to provide a source of pulsed light. In a mechanical portion, system 400 comprised an X-Y positioning table 410 and a plate holder 412 as an interface with sensor plate 20. An electronic subsystem 414 provided the functions previously disclosed for signal conditioning and for A/D conversion, i.e. circuits 204 and subsystem 208', seen in FIG. 10. An Intel 486 based personal computer 416 with sixteen megabytes of random access memory was used for programming control of mechanical controller 428 and optics controller 430. A light emitting diode with associated optics 432 was successfully tested as an optional pixel-sampling light-producing source.

Light source for laser 402 was an Omnichrome argon ion 488 nanometer wavelength laser modulated by a Neos 218080-1.25AM modulator to produce pulses of light each having a pulse width from one microsecond to twenty microseconds. Optics subassembly 406 provided ability to focus a spot of light upon a plate 20 variably to a minimum diameter of nine microns. Fiber optic interface and cable transmitted pulsed light to a movable arm of X-Y positioning table 410 whereby plate 20 was scanned one pixel at a time. Each electrical signal emanating from a scanned pixel was amplified and digitized via electronic subsystem 414. Signals were first amplified by an EG&G 142B operational amplifier and converted to digital format using a Data Translation 12 bit DT2812 A/D converter.

Using calibrated x-ray imaging standards, images having better than 20 lp/mm were demonstrated. Also, a dynamic range in excess of that achievable by film based systems was demonstrated by imaging an aluminum step wedge imaging standard having eight x-ray gray scale levels. Film images of the same step wedge standard showed only differences among four levels or steps while images using system 400 clearly showed recognizable gray scale images of all eight steps. Sensitivity of system 400 showed both a reduced required radiation exposure to achieve a predetermined image quality and a reduced amount of radiation absorbed to achieve the same purpose. As an example, an exposure of one roentgen was measured for a film system in one test providing a given image quality which compared to 235 milliroentgens for the same image quality using the described system. Also, mean glandular dose calculated in the test was 0.134 cGy for a film test compared to 0.85 cGy for system 400.

However, for a plate 20, having a thickness previously disclosed, time to process a single pixel signal was on the order of twenty-five microseconds. For images having 20,000,000 to 115,000,000 pixels (numbers compatible with high resolution chest x-ray and mammographic x-ray images, respectively), a single channel readout would require 500 to 2,000 seconds to process. Note that these times were based upon signal processing time alone and did not take into account any mechanical delays.

Times which might range from eight minutes to one half hour are considered excessive, even for very high resolution images and likely for that reason, are not commercially viable. Acceptable time to process an image is estimated to be shorter than two minutes, leading to a definite need for parallel or simultaneous multipixel processing.

Reference is now made to FIGS. 17–28 wherein, a scanning system involving a novel multichannel scanner 500 which performs as scanning system 30, seen in FIG. 14, is disclosed. In block diagram format in FIG. 17, scanner 500 is seen to comprise a light source 502, a drum 504 having a helical light-transmitting pattern of slits 506 exteriorly disposed thereon, optics 508 for producing a plurality of concurrent light beams and a controller 510 for controlling position and rates of translation and rotation of drum 504. Further scanner 500 comprises a modulator (not shown) to control period and frequency of pulses emanating from light source 502. All mechanics and controls are used in the scanning of a sensor plate 20.

Key to operation of scanner 500 is the unitary structure of drum 504. As seen in FIGS. 18–22, drum 504 (see FIG. 19) comprises a generally opaque surface 512 interrupted at regular intervals by helical light-transmitting slits 506. As seen in FIGS. 19 and 21, drum 504 is a part of a general light delivery system 520. As best seen in FIG. 21, light delivery system 520 comprises drum 504, an elongated light source 522, a central mounting housing 524, an elongated cylindrical meniscus lens 526, an elongated piano convex cylindrical lens 528, a lens holder 530, a coated precision BK-7 glass optical slit 532 and an array 534 of large diameter gradient index rod lenses, each being generally numbered 536.

Light source 522 preferably comprises a linear light emitting diode (LED) array 538 including a plurality of linearly disposed surface mounted LED's, which may be model NSCB1000 LED's, manufactured by Nichia America, 1006 New Holland Avenue, Landaster, Pa. Generally, LED's of array 538 are pulsed at a frequency which correlates with a predetermined pixel illumination period and readout rate in accordance with resolution and image processing desired for recovering an image disposed upon a plate 20. As seen in FIG. 22, light emanating from array 538 is collected and focused by lenses 526 and 528 upon an internal surface 540 of drum 504. Light is transmitted outward from surface 512 wherever light from lens 528 is coincident with a portion of light transmitting helical slits 506.

The thus produced individual rays of light are henceforth further trimmed by optical slit 532, which, as seen in FIG. 22, is disposed as an attached part of optical slit imaging lens housing 542. In combination, all optics of system 520 are sized and spaced to deliver light rays, individually numbered 521 in FIG. 19, to produce a predetermined spot size of light upon a light receiving surface, such as an outer surface of layer 102, of a sensor plate 20. As an example, for a resolution of 20 lp/mm, the spot size should not exceed 25 microns. Note that, if a light ray departing array 534 (in FIG. 22) and impinging upon the outer surface of sensor plate 20 is generally frustoconically shaped, by varying the distance between array 534 and the receiving surface of plate 20, spot size is varied. Also, within limits well known to those skilled in optical design art, spot size in one linear dimension is varied by changing width of slit 532. Benefits derived from varying spot size is addressed in more detail hereafter.

Reference is now made to FIG. 19 wherein light delivery system 520 is disposed within a translation and control assembly 550. Assembly 550 provides for X-Y axis scanning of a plate 20. Y-axis (see arrow 552) control is preferably accomplished by rotating a pair of lead screws 554 and 556 concurrently in the same direction. In the embodiment of FIG. 19, Y-axis positioning determination is provided by a Y-scan servo motor/encoder assembly 558 for lead screw 554. Likewise, lead screw 556 is accurately driven to follow lead screw 554 through operation of a timing belt assembly 560. Such lead screw and timing belt drives are commonly used for precise single axis positioning devices.

X-axis translation (in a direction indicated by arrow 562) and control is provided by rotating drum 504 which translates light transmitting sections of helical slits 506 across light steering pathway of the optics of light delivery system 520. The rate of X-axis translation is determined by pitch of helical light transmitting slits 506. Accuracy of the spot of illumination of each pixel is maintained in tight precision relative to illumination of spots of other pixels by the precision of helical slits 506. For this reason, it is very important to maintain a very high accuracy of slit 506 pattern formation upon drum 504, such as by laser milling.

Rotational drive of drum 504 is preferably provided by a direct drive torque motor 564. Accurate angular position of drum 504 is provided via an x-scan digital encoder assembly 568. Drum system 520 is preferably affixed to assembly 550 by a pair of linear ball bearing block and rail assemblies 570 and 572. Care must be taken to assure that mounting of assembly 550 and distance from drum system 520 remains true and parallel to a predetermined plane (such as plane 574, defined to be the plane where an outer layer or reading surface of layer 102 of a plate 20 is disposed for readout). Drive motors, mechanical interfaces and position and motion detecting encoders which meet accuracy and precision requirements for assembly 550 and system 520 are known and available in current art, including but not limited to X-Y plotters.

As is well known in the art of optical sampling of a sensor plate, great care must be taken to assure both damping of and isolation from elements which can cause microphonic noise. For this reason, it is preferred that assembly 550 have a mounting frame 580 which is sufficiently massive to preclude transmission of microphonic noise to system 520. Similar care should be taken to assure that plate 20 is isolated from all mechanically originated noise while processing an image.

Referring once more to FIGS. 19 & 21 with a focus upon housing 524, the optical pathway from LED array 538 through lens array 534 is generally parallel with a line which runs orthogonal to the long axis of drum 504 and which is fixed in space relative to drum 504. In combination, lenses 526, 528 and 536 act to sufficiently diffuse light from LED array 538 such that light impinging upon plane 574 is practically uniform in illumination while focusing light passing through the helical slit 506 is focused to provide a plurality of spots of predetermined size and separation. By pulsing LED array 538 (as an example, pulsing for five microseconds for each pixel), each light pulse is of known duration, thereby limiting illumination to a precise area of a plate 20 and minimizing cross-talk between pixels. While in use, housing 524 is centrally and axially disposed inside drum 504 such that light passing outward through lens 528 is partially obstructed by material of surface 512 which is between light transmitting segments of helical slits 506. For the purpose of maintaining a precise alignment between drum 504 and housing 524, housing 524 preferably comprises a steel pivot bearing shaft 582 which is juxtaposed a portion of a direct drive torque motor 564 causing drum 504 to rotate precisely about housing 524. In this manner, as light transmitting portions of helical pattern are aligned between lens 528 and plate 20, a plurality of predetermined single pixel areas are illuminated for sampling.

Note, that it is possible to sample every pixel area of a plate 20 with a single-lined helical pattern on a drum 504 rotating at a sufficiently high speed to rotate one cycle for each line traversed during Y direction travel of assembly 520. However, when traversed lines are but 25 microns apart, and it is desired to process an image having a Y dimension of 254 millimeters in approximately a minute and a half, rotational velocity of drum 504 must be in the range of 8,200 revolutions per minute, a speed which may be considered excessive for stable drum 504 operation. For this reason, it is preferable to replace a single-lined helical pattern with, as an example, a pattern which has sixteen interposed parallel lines disposed about drum 504. Other helical patterns with different numbers of interposed parallel lines may be used within the scope of the invention. In the example of a ninety second image processing time for a 198 by 254 millimeter image, using a sixteen line helical image pattern, the following system parameters produce a pixel size of 25 microns:

| Parameter | Value |
| --- | --- |
| Drum 504 diameter | 63.5 millimeters |
| Helical slit 506 width (nominal) | 0.050 millimeters |
| Number of interposed helical slits | 16 |
| Number of cycles/each helical slit | 2 |
| Number of light beams | 32 |
| Y Velocity/drum 504 rotation | 0.4 millimeters |
| Drum 504 revolutions/second | 8.204 |
| Drum revolution/line | 22.5° |

-continued

| Parameter | Value |
| --- | --- |
| Seconds/line | 0.008858 |
| Number of segments of plate 20 | 62 |
| Pixels/segment | 128 |
| Sample pulse width (of LED array 538) | 5 microseconds |
| Optical beam width | 21.4 microns |
| Light frequency (pulses per second) | 33.604 |

Figure 25:
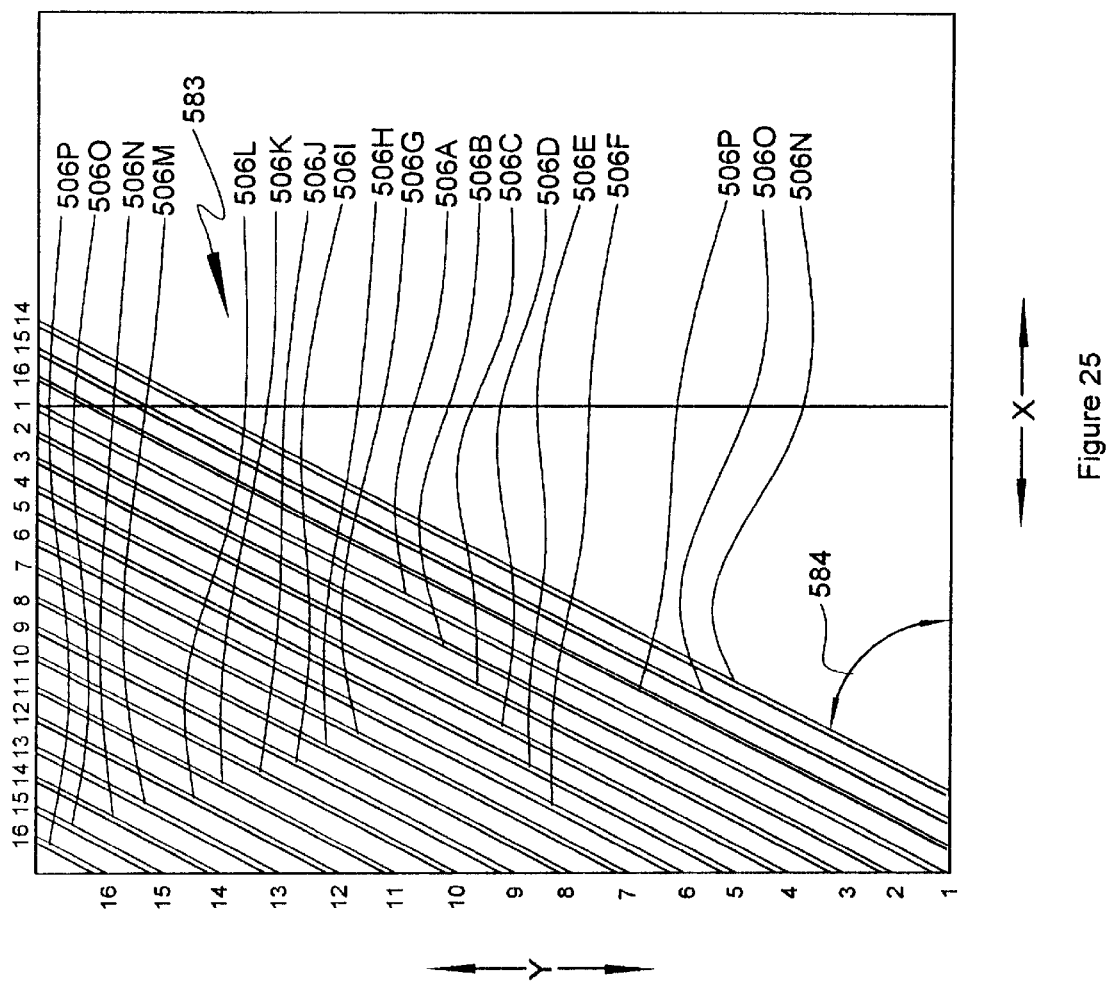
FIG. 25 is a graphic showing angle of a plurality of helical optical paths disposed upon the surface of the drum.

An X-Y linearized plot 583 of helical pattern of slits 506 is seen in a linear format in FIG. 25. The Y coordinate represents drum 504 circumference, which in this example is 199.491 millimeters. The X coordinate represents the long axis of drum 504 and shows a pattern of 16 interposed parallel slits 506A-P in an axial length of 102.4 millimeters inscribed across surface 512. The pattern of helical slits 506 is truncated after slit 506P for clarity of presentation of cyclic repetition of slits 506. Coordinates of plot 583 are circumference of drum 504 along the Y-axis, the circumference of this example being 199.491 millimeters, and axial length along the X-axis, which is 102.4 millimeters per 360° for each complete helical turn about drum 504. Note that angular pitch (indicated by line and arrows 584) is 62.828°. Of course, other numbers of interposed lines and values of angular pitch may be used within the scope of the invention.

Due to angulation of each helical line 506 and relative movement of drum 504 relative to a plate 20 being read, an illuminated spot 590 illuminated by a light ray or beam 521 is shaped more in the form of a parallelogram than as a circle as seen in FIG. 20. It should be noted also that there is a blurring of each optical spot of a light beam impinging upon a surface 102 (or 102') due to continuing X-Y travel of drum 504 relative to a pixel on a static plate 20 while a light pulse is illuminated (e.g. for 5 microseconds). For this reason, an optical beam width of approximately 21.4 microns is required to read a pixel having an effective 25 micron cross section without effects of blurring due to relative drum 504 to plate 20 movement.

As disclosed above, drum 504 is an optically permeable hollow cylinder with a generally opaque surface 512. Drum 504 should made from a dimensionally stable material such as Pyrex, quartz or a polycarbonate. Opaque surface 512 may be formed by a coating of Chromium or Inconel. Etching of slits 506 may be performed using precision laser, etching or mechanical abrasion. It may be preferable to form an elongated lens along the surface of each slit 506 to aid in focusing each light ray 521 (seen in FIG. 19).

All drum 504 movement should be smooth and free of extraneous noise. For this purpose, a DC servo motor or a direct drive torque motor is preferred for motor 564. As an example an Inland Motors P/N 3375-057 motor may be used. Torque motors are preferred due to very low cogging and exacting precision positioning characteristics. Also, exceptionally smooth continuous control is achievable without an acceleration or deceleration between brush contacts, which is an inherent result of mode of winding of the motor, which has approximately thirty to forty brushes with different poles to assure smooth operation. Direct coupling of these motors safeguards against both backlash and hysteresis characteristics between drum 504 and motor 564.

Two large bearings, such as an NPB or KB (which is a thin race instrument bearing) should be installed at each end of drum 504 to assure precision, smooth operation. A bearing block may be inserted into drum 504 on the side of motor 564 and centered where it is pivotally joined to steel pivot bearing shaft 582, permitting drum 504 to rotate about central optical system mounting housing 524. An aluminum bearing assembly should be placed on the end of drum 504 which is distal to motor 564 and bonded or otherwise securely mechanically affixed to drum 504. The bearing assembly preferably should have a pivot bearing disposed inside and a large in-race ball bearing assembly in permitting smooth rotation.

Figure 18:
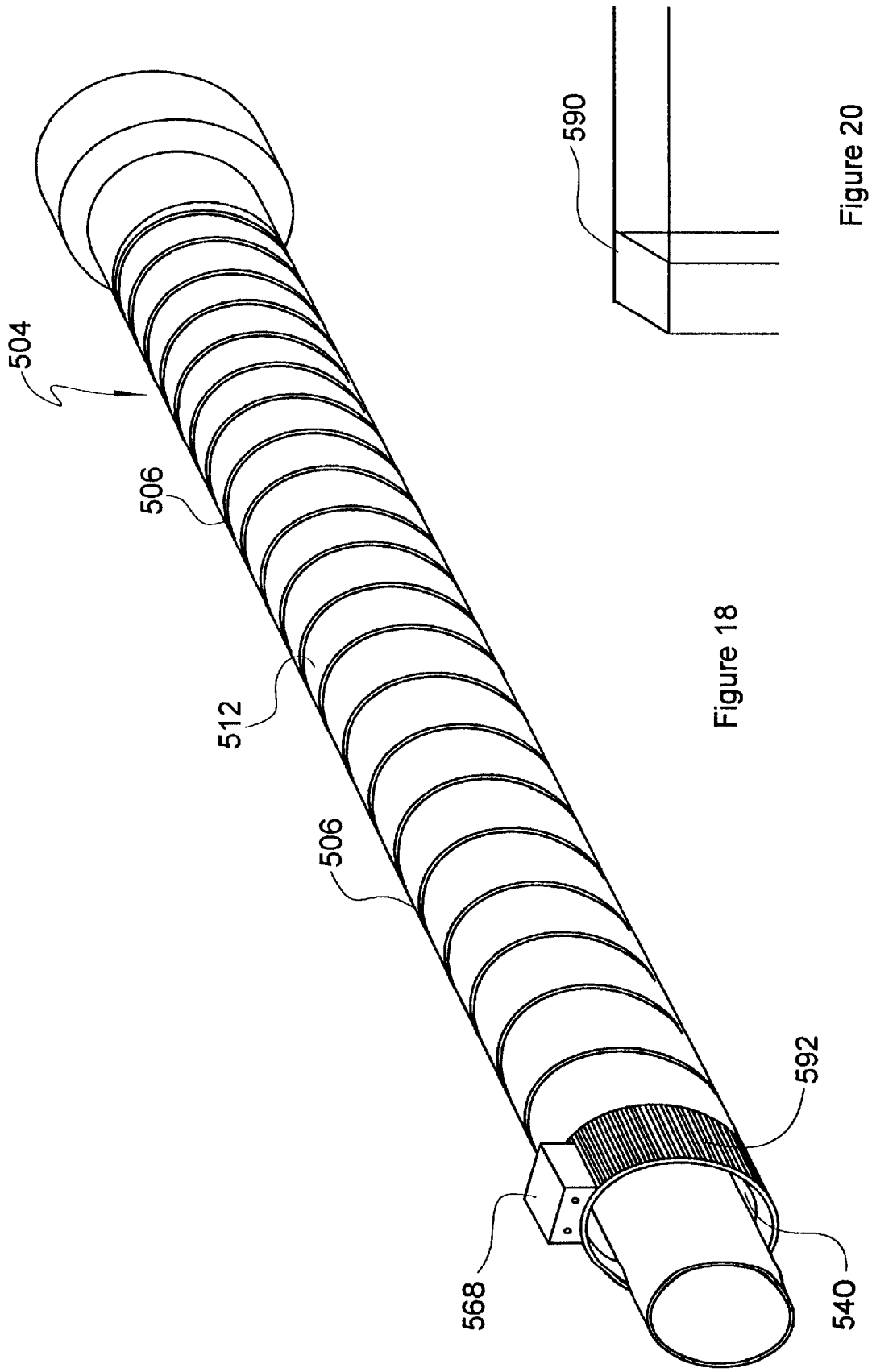
FIG. 18 is a perspective of a drum or cylindrical scan tube which is part of the digital image processing system of FIG. 17.
Figure 19:
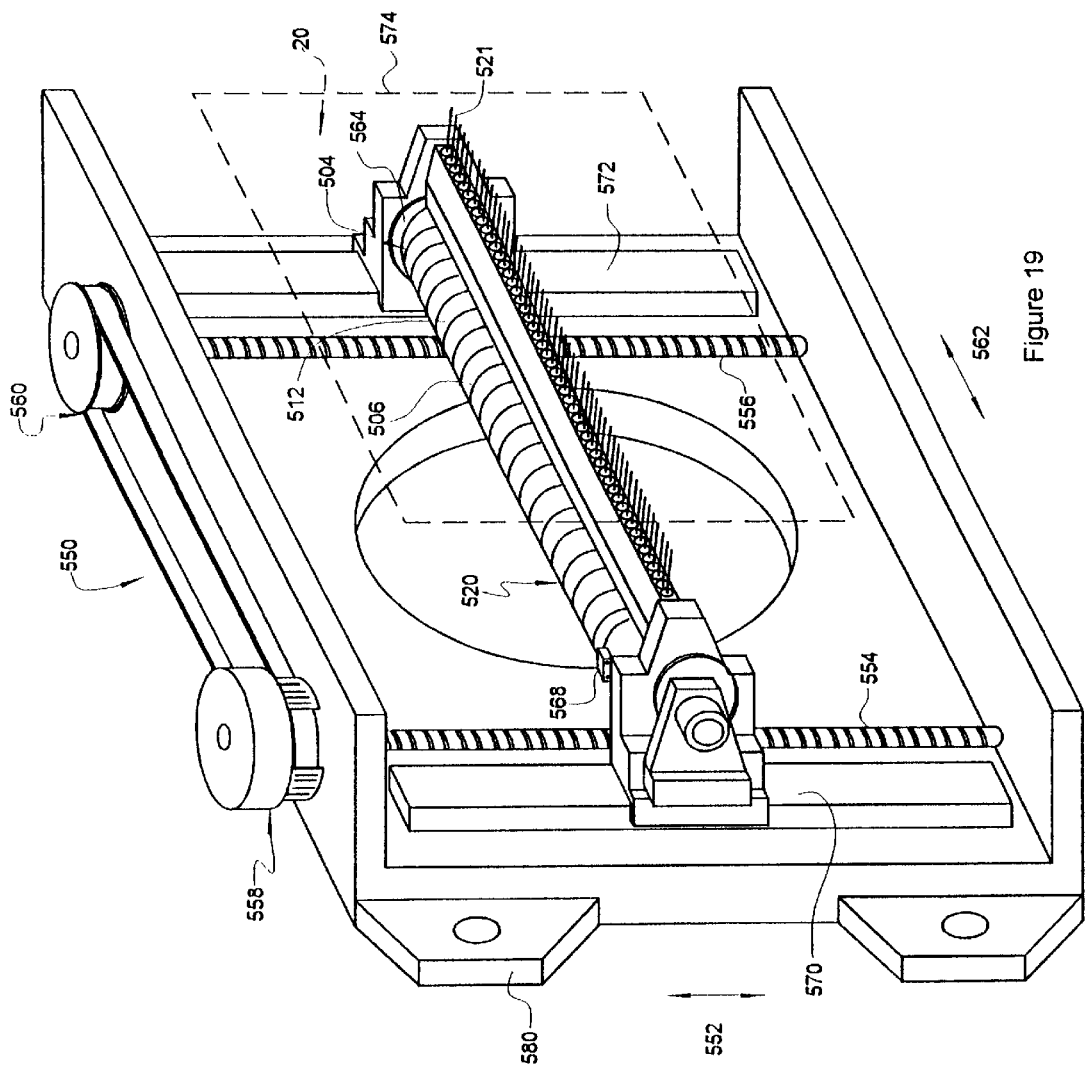
FIG. 19 is a perspective of a multiple light beam projector which comprises the drum of FIG. 18 for the purpose of simultaneously reading a plurality of pixel data from a sensor plate.

On the end of drum 504 distal from motor 564 is a series of encoder lines 592, as seen in FIG. 18, for detection by encoder assembly 568. The encoder assembly should have sufficient resolution to determine circumferential coordinates of drum 504 within plus or minus two microns.

Means for fabricating and installing encoder lines 592 and encoder assemblies are commercially available within the state of the digital control art.

The combination of elongated cylindrical meniscus lens 526 and elongated piano convex cylindrical lens 528 form a spatial filter and a condenser assembly. Meniscus lens 526 collects maximum angular gradients of light from LED array 538 to increase light out efficiency. As light passes through lens 528, it is focused upon slit 532, forming a single axis spatial filter.

For twenty lp/mm precision, slit 532 should be approximately twenty microns wide. Lens array 534 forms a gradient index relay lens and provides a single element relay system for transferring each of the thirty-two light beams of the exemplary assembly disclosed above from optical slit 532 to a plate 20 being scanned. In this example, each index rod lens 536 is five millimeters. Index rod lens 536 should be designed to provide an evenness of illumination across the linear surface of array 534 which varies by not more than 0.5% from peak illumination, after calibration. Such lens arrays are currently commercially available, and may be acquired from The Gradient Lens Corporation, Rochester, N.Y. Other lens combinations which may be used within the scope of the invention comprise vertical cylindrical planoconvex arrays, a piano-convex spherical lens array and a double optical spheres lens array.

Figure 26:
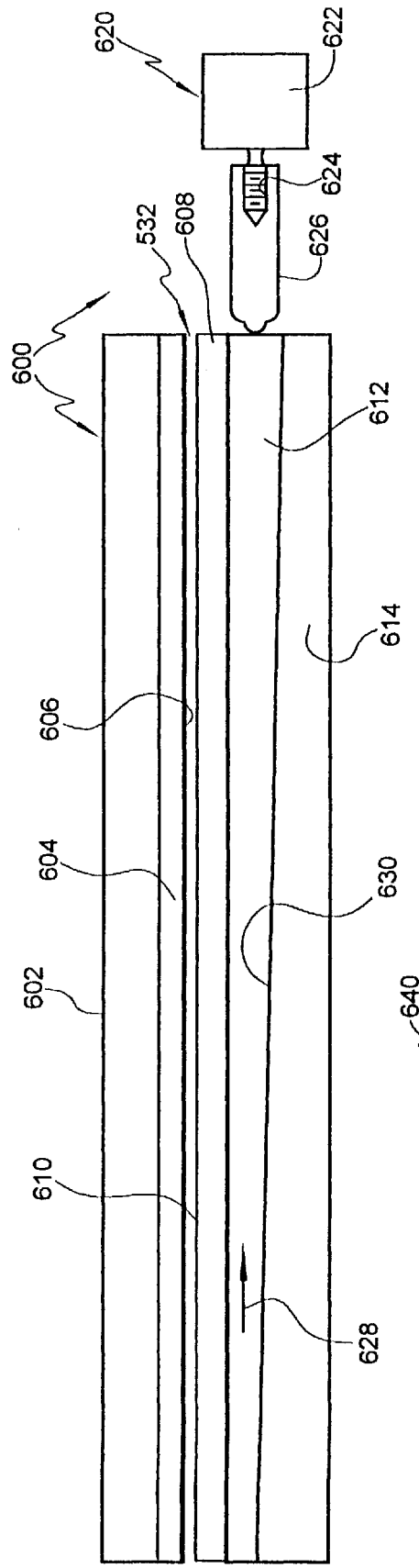
FIG. 26 is a cross section of a variable slit used as a programmable optical stop in a variable resolution drum-based readout system.
Figure 27:
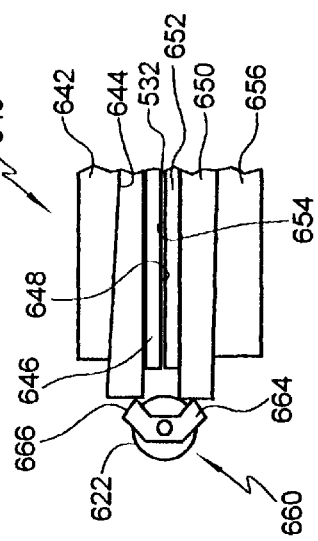
FIG. 27 is a cross section of a pivot arm used to vary width of the variable slit of FIG. 26.

Of course, if it is desired to have a single instrument operate efficiently over a variable resolution range, such parameters as light beam 521 on-time and illuminated spot-size 590 should be controllably changeable. Such controls may be accomplished by moving optical slit imaging lens housing 542 toward and away from plate 20 in predetermined increments. In addition, slit 532 width may be controllable widened or thinned. An exemplary apparatus 600 for changing slit 532 width is seen in FIGS. 26 and 27. Apparatus 600 comprises a stationary mounting plate 602, a first blade 604 comprising a sharp edge 606, a second blade 608 comprising a sharp edge 610, a spring loaded, angled slider 612 and an angled guide wedge 614. In addition, apparatus 600 comprises a slider 612 drive unit 620 which comprises a stepper motor 622, a pitch screw 624 and a non-rotational actuator screw nut 626 which is in contact with slider 612. In addition, drive unit 620 would preferably comprise an encoder system (not shown) or other sensor mechanism to provide slit width measurement feedback to a controlling processor, such as processor 210.

Slider 612 is spring loaded in direction of arrow 628 against actuator nut 626 such that rotation of pitch screw 624 causes slit 532 width to narrow or broaden at a predetermined rate relative to angular rotation of motor 622 and screw 624 due to a sloped interface 630 disposed between slider 612 and wedge 614. By this method, slit 532 is constrained to remain parallel with array 534.

In some cases, it may be desired to have slit 532 remain symmetrically and centrally disposed relative to light paths traced from lens 528. In such cases, another apparatus 640 for varying slit 532 may be employed. As seen in FIG. 27, slit 532 is symmetrically sandwiched within apparatus 640 which comprises in seriatim a first static outside housing 642, a wedge 644 securely affixed to a blade 646 having a true linear edge 648, a second wedge 650 securely affixed to a blade 652 having a true linear edge 654 which is parallel to edge 648 and a second static outside housing 656. Apparatus 640 further employs a drive unit 660 which comprises a stepper motor 622 and slit governor arm 664. Arm 664 is pivotally affixed to wedge 644 at junction 666 and to wedge 650 such that angular rotation of motor 622 in a first direction narrows slit 532 and rotation in a second direction widens slit 532. Of course, such widening and narrowing should be measured and known. As one skilled in digital control understands, such is generally accomplished through use of an encoder, not shown.

Figure 23:
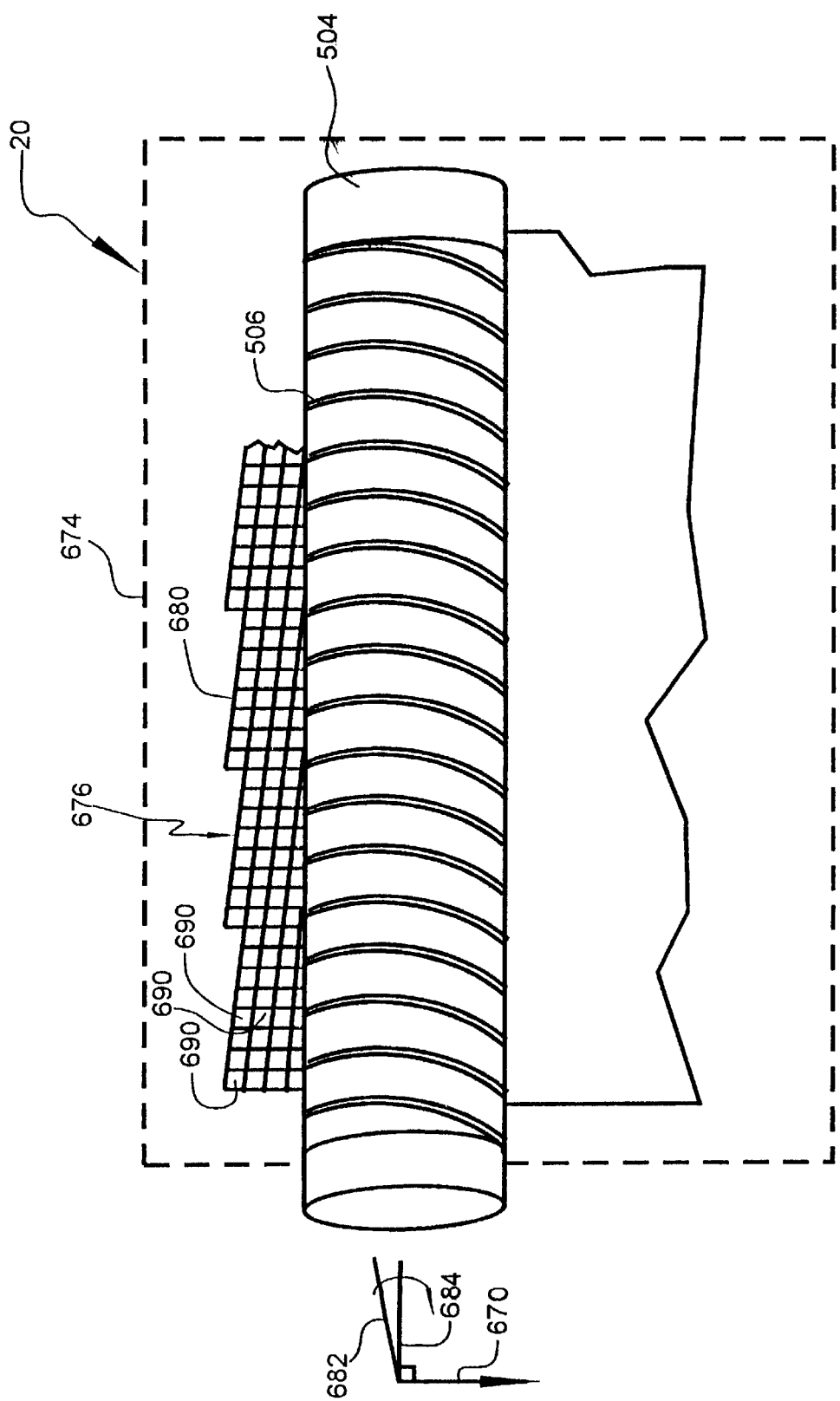
FIG. 23 is a graphic showing pattern of data read by a traveling and rotating drum when the longitudinal axis of the drum is disposed perpendicular to direction of translational travel of the drum scan tube.

In addition to blurring and geometric distortion of individual pixels due to relative movement and angulation of drum 504 parts relative to plate 20, pixels read by a drum which is orthogonally oriented (along an X-axis) relative to direction of travel of the drum (along a Y-axis) yields non-orthogonal pixel arrays. As is seen in FIG. 23, travel of drum 504 is in direction of arrow 670. As seen in FIG. 23, angle of rotation 672 of drum 504 is at a right angle with axis of rotation arrow 672. Disposed beneath drum 504 is plate 20 generally schematically bounded by dashed line 674. Each successive pixel, generally numbered 680, is offset by pixel sampling time and therefore drum travel to produce a non-orthogonal array, as demonstrated by exemplary array 676 wherein each pixel 680 is offset from its left-right neighbors by an increment which is equal to Y travel of drum 504 during a single sampling period.

Figure 24:
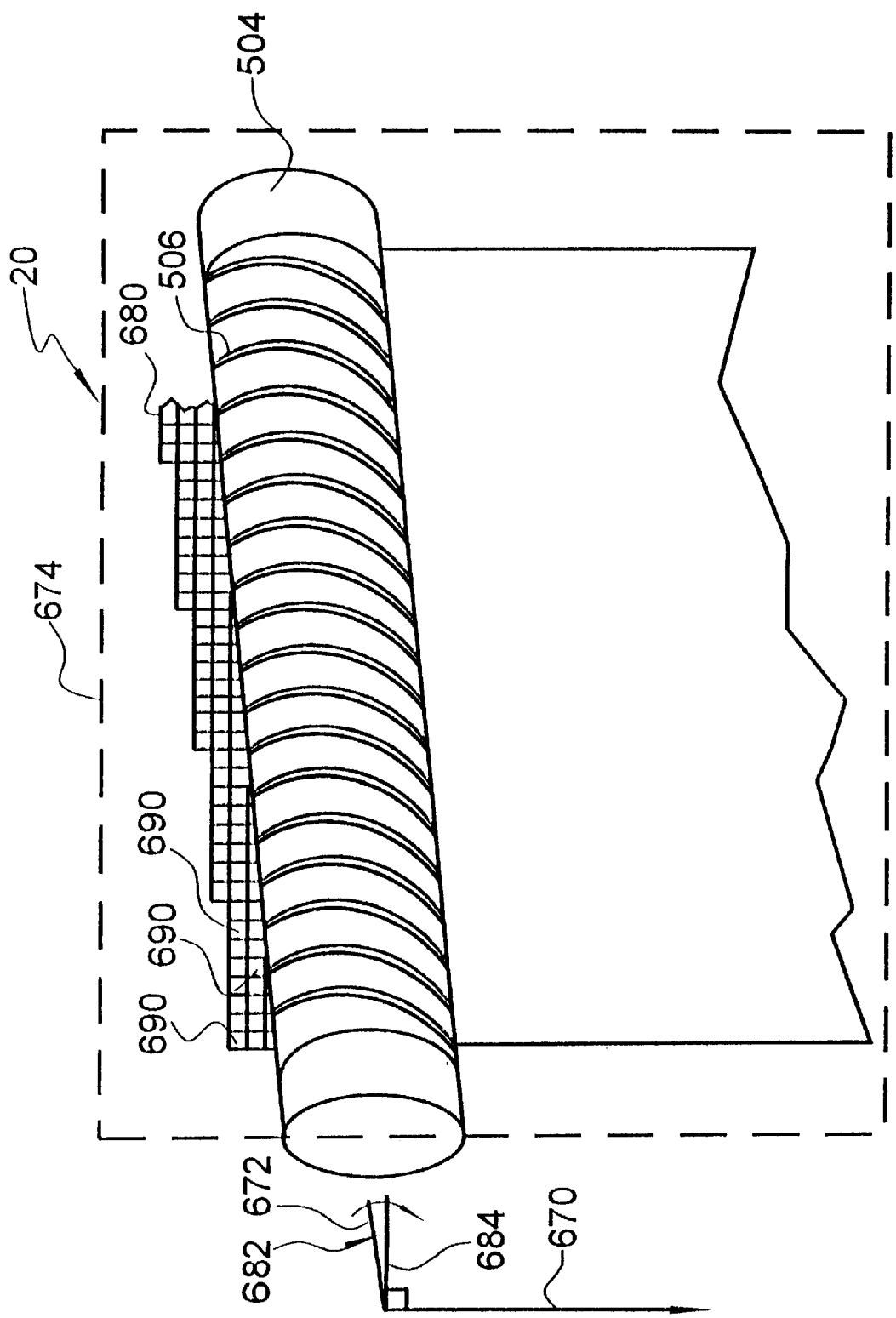
FIG. 24 is a graphic showing orthogonal pattern of data when the drum scan tube is selectively angularly disposed relative to direction of translational travel of the drum scan tube.

As seen in FIG. 24, an orthogonal array 680 is generated when axis of rotation 672 of drum 504 is disposed at a predetermined angle 682. The axis of rotation 670 is angularly offset from a line 684 which is perpendicular to direction of travel indicated by arrow 670. Angle 682 may be precalculated, such as by Equation 2 below:

$$\text{Angle } 682 = \arcsin(n_b/n_p) \qquad \text{Eq. 2}$$

where: $n_b$ is the number of light beams 521 concurrently emitted by assembly 520. (See FIG. 19)

$n_p$ is the maximum number of pixels (e.g. pixels 690 in FIG. 24) per line.

As an example, for thirty-two concurrent beams scanning a plate and sixty-two segments in a plate with one hundred twenty-eight pixels areas 690 per segment, angle 682 is 0.00403228 radians.

Critical to removing built in noise factors, which may result from manufacturing or aging-related material parameters such as inhomogeneity in transparency of the indium tin oxide layer 102, changes in spatial intensity of LED array 538, anomalies in lenses (e.g. lens 526, 538 and 534), variations in gains of amplifiers and departures from standards of analog to digital converters lead to artifacts and image deficiencies which are correctable by application of proper calibration techniques. Calibrating is well known in the medical instrumentation art and opportunity to minimize image deficiencies should not be limited by the list above. For this purpose, it is advisable to provide means for calibrating both system and plate characteristics upon each plate 20. Referring to FIG. 13, for example, a plate 20 identifying code 800 (similar in form and function to a bar code) may be applied to each plate such that inherent plate anomalies may be recorded and subtracted from scanned and processed data to improve image quality. Other markers such as gray scale patterns (such as pattern 802 may be added in strategic non-image recording places for purposes of calibrating optical and electronic parts. Landmarks, such as marks 804, 806 and 808 may be used to provide geometric reference for pixel coordinates. Such landmarks are particularly useful when correlating pixel coordinates on dual sided plates, such as configurations 120 and 130 (seen in FIGS. 4 and 5). Also, such landmarks permit correlation of relative drum 504 to plate 20 orientation for initializing operation of multiplexer 207.

Figure 17:
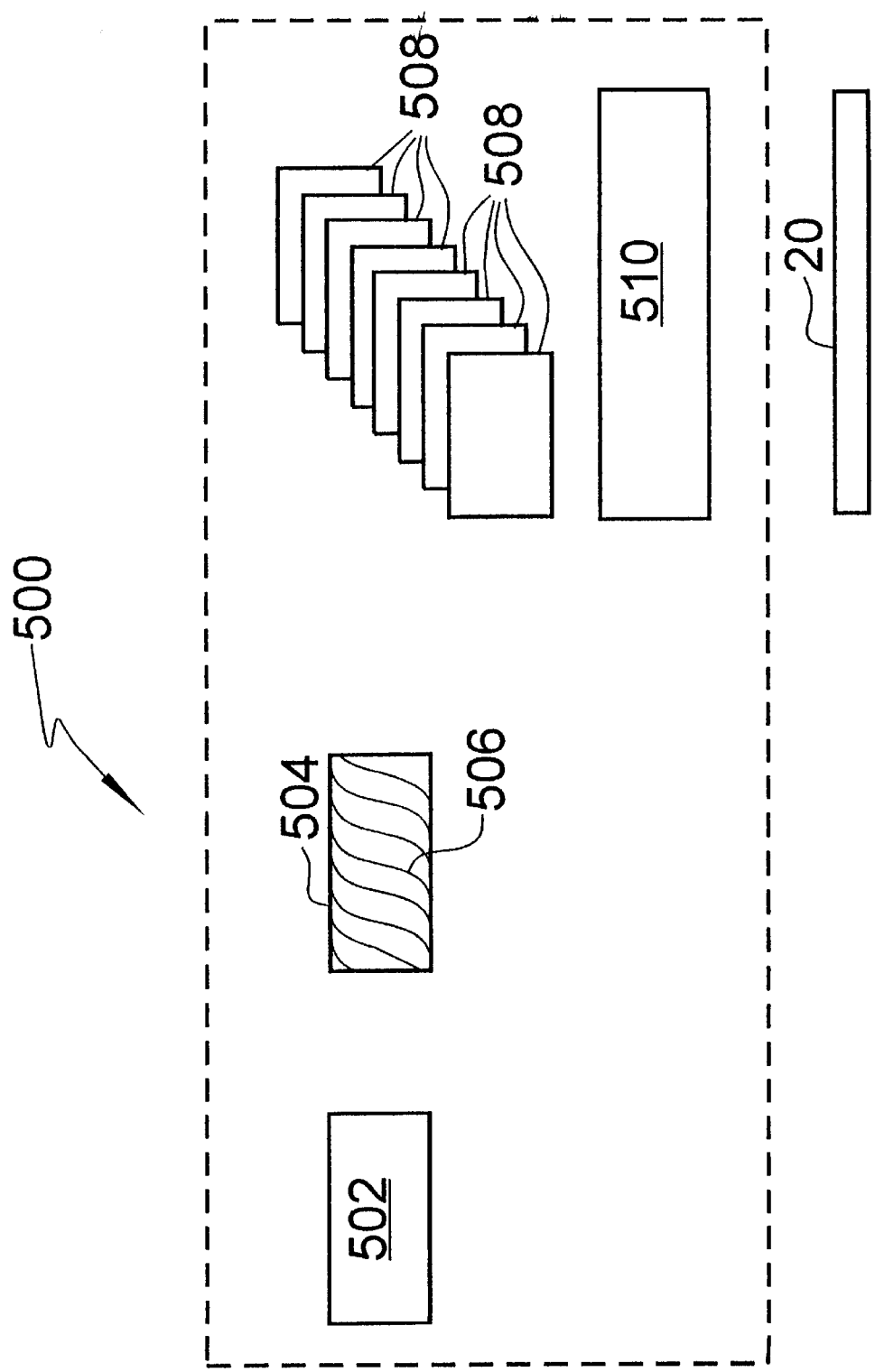
FIG. 17 is a block diagram of a mechanical portion of a digital image processing system.

Reference is now made to FIG. 28 wherein a block diagram of a system 900 comprising an image processing system 902 similar to image processing system 200 seen in FIG. 10, a scanner 904 similar to scanner 500 seen in FIG. 17 and a central control and image processor 210 similar to image processor 50 seen in FIG. 14. System control and coordination is performed by central processor 906. A plurality of digital control and data lines generally numbered 908 are used to systematically control rotational and linear velocity of drum 504 through controller 510. Synchronized with drum 504, light source 502 is pulsed to excite each pixel to expose a regular pattern on a plate 20. Likewise, control circuits within image processing subsystem 902 are synchronized to integrate and amplify, sample and hold and convert from analog to digital each pixel when excited. An array of pixels is first captured in one (or more) processors 210 and then communicated to central processor 906 for permanent storage and display. It should be noted that drum 504 preferably comprises one helical strand for each two segments, although other helical patterns may be used within the scope of the invention. The number of segments may be increased or decreased to change image processing rate. Of course each change in numbers of segments results in a proportionate change in numbers of amplifiers 150 and signal conditioning circuits 204 and in numbers of A/D channels required.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A substantially planar, layered photon sensor plate and light source combination, said combination being used for producing a filmless photon image comprising a digital array of pixels, said combination comprising:

the plate comprising:
a plurality of layers comprising in seriatim:
a first layer, having an exposed external flat surface, which is electrically conductive and at least transparent to light frequencies used to excite a photoconductive layer;
an insulating layer in physical contact with the first layer;
the photoconductive layer in which a latent form of the image is stored;
a blocking layer;
a second conductive layer;
said first layer comprising at least three elongated, conductive segments linearly disposed along one dimension of said plate, each segment being displaced and electrically isolated one from the other;

one electrical output from each segment;

a plurality of electrical pre-amplifiers for amplifying signals from the segments;

means, for multiplexing signals through the electrical outputs from preselected adjoining segments such that at least signals emanating from pixels resident on a portion of each adjoining segment and pixels disposed between the segments are processed through at least one preamplifier;

electrical pathway and connection means for transmitting amplified signals for processing external to the plate; and said light source comprising at least two light beams for simultaneously applying separate pixel sized rays of light to said first layer for the purpose of concurrently reading a plurality of pixels from said plate, said beams being displaced substantially in the direction of the one dimension to read pixels in seriatim from said plate.

2. A combination according to claim 1 wherein each segment comprises a singular connection to an electrical pre-amplifier.

3. A combination according to claim 1 wherein each segment comprises a connection to the signal multiplexing means.

4. A combination according to claim 1 wherein said second conductive layer comprises aluminum.

5. A combination according to claim 4 wherein said second conductive layer and said blocking layer comprise aluminum and aluminum oxide, respectively and are formed by the same part.

6. A combination according to claim 1 wherein said photoconductive layer comprises amorphous selenium.

7. A combination according to claim 6 wherein said amorphous selenium layer has a thickness in the range of 10 to 500 microns.

8. A combination according to claim 1 wherein said first layer comprises indium tin oxide.

9. A combination according to claim 8 wherein said insulating layer is a polymer.

10. A combination according to claim 1 further comprising an intensifying screen disposed to cover the exposed external surface of the first layer.

11. A combination according to claim 1 further comprising a calibration pattern disposed as an integral part of the plate.

12. A dual-energy radiography sensor plate by which three x-ray images, comprising a standard x-ray image, a high energy image which, as an example, may be the result of imaging mostly bone mass and an image provided by calculating the difference between the standard image from the high energy image, are derived, the sensor plate comprising:

an electrically conductive, x-ray absorbing plate having a top side and a bottom side and a predetermined thickness, said thickness providing a means for separating higher energy x-rays from lower energy x-rays;

a first photoconductive layer superiorly disposed to said top side to produce a second top side;

an electrically insulating layer disposed upon said second top side to form a third top side;

a semi-transparent electrically conducting layer disposed upon said third top side;

a second photoconductive layer disposed inferiorly to said bottom side to produce a second bottom side;

an electrically insulating layer inferiorly disposed to said second bottom side to form a third bottom side; and a semi-transparent electrically conducting layer inferiorly disposed upon said third bottom side.

13. A dual-energy radiography sensor plate according to claim 12 further comprising a plurality of electrical connectors upon the electrically conducting layers and x-ray absorbing plate for the purpose of transmitting sensor detected signals to an image processing system.

14. A dual-energy radiography sensor plate according to claim 12 wherein said first photoconductive layer comprises selenium.

15. A dual-energy radiography sensor plate according to claim 12 wherein said second photoconductive layer comprises selenium.

16. A dual-energy radiography sensor plate according to claim 12 wherein said electrically insulating layers each comprise a layer of a polymer.

17. A dual-energy radiography sensor plate according to claim 12 further comprising a pair of intensifying screens, with one screen disposed against an exterior surface of each semi-transparent electrically conducting layer.

18. A method for making a filmless, dual-energy radiography sensor plate by which three x-ray images, comprising a standard x-ray image, a high energy image of mostly bone mass and an image provided by subtracting the standard image from the high energy image, are derived comprising the following steps:

providing an electrically conductive, x-ray absorbing layer having a top side and a bottom side and a predetermined thickness, said thickness providing a means for separating higher energy x-rays from lower energy x-rays;

each top side and bottom side comprising a blocking layer component;

applying a first photoconductive layer to said top side to produce a second top side;

applying an electrically insulating layer upon said second top side to form a third top side;

applying a semi-transparent electrically conducting layer upon said third top side;

applying a second photoconductive layer to said bottom side to produce a second bottom side;

applying an electrically insulating layer to said second bottom side to form a third bottom side; and applying a semi-transparent electrically conducting layer inferiorly upon said third bottom side.

19. A method according to claim 18 further comprising steps of peripherally disposing a plurality of electrical connectors upon the electrically conducting layers and x-ray absorbing layer for the purpose of transmitting sensor detected signals to an image processing system.

20. A method according to claim 18 wherein said applying steps comprise vacuum depositing of material.

21. A method according to claim 18 wherein said first photoconductive layer applying step comprises applying a layer of selenium.

22. A method according to claim 18 wherein said second photoconductive layer applying step comprises applying a layer of selenium.

23. A method according to claim 18 wherein said electrically insulating applying steps comprise applying a polymer.

24. A method according to claim 18 further comprising a step for constructing said sensor whereby planar outside surfaces of said sensor are accessible to be read independent of one another.

25. A method according to claim 18 further comprising steps for segmenting each of said semi-transparent electrically conducting layers into at least three like segments each juxtaposed the other, each segment being electrically isolated from each of the other segments.

26. A method according to claim 25 comprising additional steps providing one electrical output from each segment.

27. A method according to claim 25 comprising mounting, directly upon the plate, a plurality of electrical pre-amplifiers for amplifying signals from the segments.

28. A method according to claim 27 comprising also mounting, directly upon the plate, means for multiplexing signals through the electrical outputs from preselected adjoining segments such that at least signals emanating from pixels resident on a portion of each adjoining segment and pixels disposed between the segments are processed through at least one preamplifier.

29. A method according to claim 25 further comprising the step of making a connection between each segment and one electrical pre-amplifier.

30. A method according to claim 25 comprising the additional step of making a connection between each segment and a signal multiplexing means.

31. A method according to claim 18 comprising the step of adding an electrical connector to the plate.

32. A method according to claim 18 comprising a step of making each photoconductive layer out of amorphous selenium.

33. A method according to claim 32 comprising a step of selectively limiting the thickness of each photoconductive layer to be within a range of 10 to 500 microns.

34. An electrical system for processing signals from a segmented plate without appreciable degradation at segmentation interfaces, said system comprising:
    a substantially planar, layered photon sensor plate having two flat exterior surfaces, said plate being used for producing a filmiess photon image comprising a digital array of pixels, said plate comprising:
        a plurality of layers comprising in seriatim:
            a first layer, having an ambient exposed surface, which is electrically conductive and at least transparent to light frequencies used to excite a photoconductive layer;
            an insulating layer in physical contact with the first layer;
            the photoconductive layer in which a latent form of the image is stored;
            a blocking layer;
            a second conductive layer;
            said first layer comprising at least three elongated, planar segments linearly disposed along one dimension of said sensor plate, each segment being electrically isolated from each of the other segments;
            one electrical output from each segment;
    a scannable light source comprising a plurality of emitted photon beams which scan said plate in substantially the direction of said one dimension;
    a plurality of electrical pre-amplifiers for amplifying signals from the segments; and
    a multiplexing circuit which selectively joins electrical lines carrying signals from preselected adjoining segments such that signals emanating from pixels resident on a portion of each adjoining segment and pixels disposed between the segments are processed through a common preamplifier.

35. A method for acquiring signals from a segmented plate, without incurring appreciable degradation at segmentation interfaces, comprising the steps of:
    (a) providing an electrical system for processing signals from a segmented plate comprising:
        a substantially planar, layered photon sensor plate having two flat exterior surfaces, said plate being used for producing a filmless photon image comprising a digital array of pixels, said plate comprising:
            a plurality of layers comprising in seriatim:
                a first layer, having an ambient exposed surface, which is electrically conductive and at least transparent to light frequencies used to excite a photoconductive layer;
                an insulating layer in physical contact with the first layer;
                the photoconductive layer in which a latent form of the image is stored;
                a blocking layer;
                a second conductive layer;
            said first layer comprising at least three segments each being electrically isolated from all adjacent segments by an intersticial non-conducting boundary, said segments being referenced in adjoining sequence by numbers one, two and three;
            one electrical output from each segment;
                a plurality of electrical pre-amplifiers for amplifying signals from the segments;
                a means for multiplexing outputs signals emitted from each of said segments;
    (b) connecting segment two to one of the other two segments, for example connecting segment two to segment one;
    (c) scanning across interstitial boundary between segment one and segment two while said segments are interconnected;
    (d) thereafter disconnecting segment one from segment two while a portion of segment two only is being scanned and thereafter connecting segment two to segment three before the interstitial boundary between segment two and segment three is scanned;
    (e) scanning across interstitial boundary between segment two and segment three while said segments are interconnected;
    (f) thereafter, disconnecting segment two from segment three and repeating step (b).

* * * * *